United States Patent
Cunningham et al.

(10) Patent No.: US 10,078,082 B2
(45) Date of Patent: Sep. 18, 2018

(54) DETECTION OF FREE AND PROTEIN-BOUND NON-HUMAN GAL-ALPHA(1-3)-GAL EPITOPE

(71) Applicant: National University of Ireland, Galway, Galway (IE)

(72) Inventors: Stephen Cunningham, Galway (IE); Emily Starr, Galway (IE); Iain Shaw, Galway (IE); John Glavin, Galway (IE); Marian Kane, Galway (IE); Lokesh Joshi, Galway (IE)

(73) Assignee: NATIONAL UNIVERSITY OF IRELAND, GALWAY, Galway (IE)

( * ) Notice: Subject to any disclaimer, the term of this patent is extended or adjusted under 35 U.S.C. 154(b) by 17 days.

(21) Appl. No.: 14/434,669

(22) PCT Filed: Oct. 11, 2013

(86) PCT No.: PCT/EP2013/071367
§ 371 (c)(1),
(2) Date: Apr. 9, 2015

(87) PCT Pub. No.: WO2014/057129
PCT Pub. Date: Apr. 17, 2014

(65) Prior Publication Data
US 2016/0003839 A1    Jan. 7, 2016

(30) Foreign Application Priority Data
Oct. 11, 2012    (EP) .................................... 12188179

(51) Int. Cl.
| | | |
|---|---|---|
| *C07K 16/18* | (2006.01) | |
| *G01N 33/53* | (2006.01) | |
| *G01N 33/563* | (2006.01) | |
| *G01N 33/577* | (2006.01) | |
| *G01N 33/68* | (2006.01) | |
| *C07K 16/44* | (2006.01) | |

(52) U.S. Cl.
CPC ......... *G01N 33/6842* (2013.01); *C07K 16/18* (2013.01); *C07K 16/44* (2013.01); *C07K 2317/23* (2013.01); *C07K 2317/33* (2013.01); *C07K 2317/622* (2013.01); *C07K 2317/92* (2013.01); *G01N 2400/02* (2013.01); *G01N 2800/245* (2013.01)

(58) Field of Classification Search
None
See application file for complete search history.

(56) References Cited

FOREIGN PATENT DOCUMENTS

WO    WO-2008/057235    5/2008
WO    WO-2012/135313    10/2012

OTHER PUBLICATIONS

Paul, Fundamental Immunology, 3rd Edition, 1993, pp. 292-295.*
Rudikoff et al., Proc. Natl. Acad. Sci. USA, 79(6):1979-1983, Mar. 1982.*
Colman, Research in Immunology, 145:33-36, 1994.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
Andris-Widhopf J et al. (2000), "Methods for the generation of chicken monoclonal antibody fragments by phage display", J. Immunological Methods 242:159-181.
Bosques C J et al. (2010), "Chinese hamster ovary cells can produce galactose-alpha-1,3-galactose antigens on proteins", Nature Biotechnology 28(11):1153-1156, Nov. 2010.
Chen et al. (2000), "Genes coding evolutionary novel anti-carbohydrate antibodies: studies on anti-Gal production in alpha1,3galactosyltransferase knock out mice", Molecular Immunology, vol. 37, No. 8, Jun. 1, 2000, pp. 455-466.
Cunningham S et al. (2012), "Development of a Convenient Competitive ELISA for the Detection of the Free and Protein-Bound Nonhuman Galactosyl-[alpha]-(1,3)-Galactose Epitope Based on Highly Specific Chicken Single-Chain Antibody Variable-Region Fragments", Analytical Chemistry, vol. 85, No. 2, Dec. 6, 2012, pp. 949-955.
Galili U et al. (1998), "A Sensitive Assay for Measuring Alpha-Gal Epitope Expression on Cells by a Monoclonal Anti-Gal Antibody", Transplantation, Williams and Wilkins, Baltimore US, vol. 65, No. 8, Apr. 27, 1998, pp. 1129-1132.
International Search Report and Written Opinion (ISA/EPO) for International Application No. PCT/EP2013/071367, dated Jan. 20, 2014, 17 pages.
Kearns-Jonker et al. (2007), "Use of molecular modeling and site-directed mutagenesis to define the structural basis for the immune response to carbohydrate xenoantigens", BMC Immunology, Biomed Central, London, GB, vol. 8, No. 1, Mar. 12, 2007, p. 3.
Milland et al. (2007), "Carbohydrate residues downstream of the terminal Galalpha(1,3)Gal epitope modulate the specificity of xenoreactive antibodies", Immunology and Cell Biology Nov.-Dec. 2007, vol. 85, No. 8, Nov. 2007, pp. 623-632.
Naso F et al. (2010), "First quantitative assay of alpha-Gal in soft tissues: Presence and distribution of the epitope before and after cell removal from xenogeneic heart valves", Acta Biomaterialia, Elsevier, Amsterdam, NL, vol. 7, No. 4, Nov. 22, 2010, pp. 1728-1734.

(Continued)

*Primary Examiner* — Hong Sang
(74) *Attorney, Agent, or Firm* — Foley & Lardner LLP; Antoinette F. Konski; Peng Sun

(57) ABSTRACT

The present invention relates to the provision of antibody fragments capable of binding selectively to the Gal-α-(1→3)-Gal epitope. The invention further relates to assay systems comprising these antibody fragments for use in testing transplantation tissue for possible rejection complications. This epitope is often found on porcine tissue destined for human transplantation. The epitope is also found on biopharmaceuticals and on some infectious agents and accordingly the invention also provides assay systems for these applications.

8 Claims, 14 Drawing Sheets

Specification includes a Sequence Listing.

(56) References Cited

OTHER PUBLICATIONS

Starr et al. (2010), "Identification of a Gal alpha 1-3Gal-Specific Scfv Library", Glycobiology, vol. 20, No. 11, Nov. 2010 (Nov. 2010), p. 1519.
Yu et al. (1996), "Modulation of natural IgM binding and complement activation by natural IgG antibodies: a role for IgG anti-Gal alpha1-3Gal antibodies", The Journal of Immunology, vol. 157, No. 11, Dec. 1, 1996, pp. 5163-5168.

* cited by examiner

Figure 9

```
                            10         20         30         40
                            |          |          |          |
scFv-A4/1-259     1  QAALTQPSSVSTNPGGTVKITCSGGN-----GNYGWYQQKSPGS  39
scFv-G12/1-261    1  QAALTQPSSVSANPGETVKITCSGG-----SYHYGWYQQKSPGS  39
scFv-A11/1-263    1  QAALTQPSSVSANPGETVKITCSGGGSYGGSYYYGWYQQKSPGS  44

50         60         70         80
                              |          |          |          |
scFv-A4/1-259    40  APVTVIYSNNKRPSDIPSRFSGSKSGSTATLTITGVQVDDEAVY  83
scFv-G12/1-261   40  APVTVIYSNNQRPSGIPSRFSGSTSDSTGTLTITGVQADDEAVY  83
scFv-A11/1-263   45  APVTVIYSNDNRPSDIPSRFSGSTSGSTSTLTITGVQVDDEAVY  88

90        100        110        120        130
                        |          |          |          |          |
scFv-A4/1-259    84  FCGAYDN--TYVGVFGAGTTLTVLGQSSRSSSGGGSSGGGGSAV 125
scFv-G12/1-261   84  FCGSYDSSNTYAGIFGAGTTLTVLGQSSRSSSGGGSSGGGGSAV 127
scFv-A11/1-263   89  YCGTYDS--SYVGIFGAGTALTVLGQSSRS-GGGSSGGGGSAV 129

140        150        160        170
                              |          |          |          |
scFv-A4/1-259   126  TLDESGGGLQTPGGGLSLVCKASGFTFSSYSMQWVRQTPGKGLE 169
scFv-G12/1-261  128  TLDESGGGFQTPGGALSLVCKASGFTFSSYSMQWVRQAPGKGLE 171
scFv-A11/1-263  130  TLDESGGGLQTPGGGLSLVCKASGFTFSSYSMQWVRQTPGKGLE 173

180        190        200        210
                              |          |          |          |
scFv-A4/1-259   170  FVAGIGYSDSYTYFGPAVKGRATISRDNGQNIVRLQLNNLRAED 213
scFv-G12/1-261  172  FVAGIGNSDRYTYFGPAVKGRATISRDNGQSILRLQLNNLRAED 215
scFv-A11/1-263  174  FVAGIGYSDSYTYFGPAVKGRATISRDNGQNIVRLQLNNLRAED 217

230        240        250        260
                              |          |          |          |
scFv-A4/1-259   214  TATYYCARSADTIYGCTHPWCSADNIDAWGHGTEVIVSSTSGQA 257
scFv-G12/1-261  216  TATYFCARSGDSGNGCTHPWCSADNINAWGHGTEVIVSSTSGQA 259
scFv-A11/1-263  218  TATYYCARSADTIYGCTHPWCSADNIDAWGHGTEVIVSSTSGQA 261 scFv-A4/1-259   258  GQ  259
scFv-G12/1-261  260  GQ  261
scFv-A11/1-263  262  GQ  263
```

Figure 10

```
                                        V_L CDR 1              V_L CDR 2
  1    QAALTQPSSV SANPGGTVKI TCSGGNSYGG SYNYGNYQQK SPGSAPVTVI YSNNKRPSDI    60
  1             T           N**** *GN                         NK    D    60
  1             A           GSYGG SYY                         DN    D    60
  1             A           ***** SYH                         NQ    G    60

V_L CDR 3              Linker
 61    PSRFSGSTSG STATLTITGV QVDDEAVYFC GAYDSSNTIV GVFGAGTTLT VLGQSSRSSS   120
 61             K G        A          V F  A N**T V V        T          S    120
 61             T G        S          V Y  T S**S V I        A          *    120
 61             T D        G          A F  S SSNT A I        T          S    120 sequence                        V_H CDR 1
121    GGGSSGGGGS AVTLDESGGG LQTPGGGLSL VCKASGFTFS SYSMQWVRQT PGKGLEFVAG   180
121                          G                               T            180
121                          G                               T            180
121                          A                               A            180

V_H CDR 2                                            V_H CDR 3
181    IGYSDSYTYF GPAVKGRATI SRDNGQNTVR LQLNNLRAED TATYYCARSA DTIYGCTHPW   240
181    Y S                   N V                  Y          A TIY          240
181    Y S                   N V                  Y          A TIY          240
181    N R                   S L                  F          G SGN          240

241    CSADNIDAWG HGTEVIVSST SGQAGQ   266
241           D                       266
241           D                       266
241           N                       266
```

A
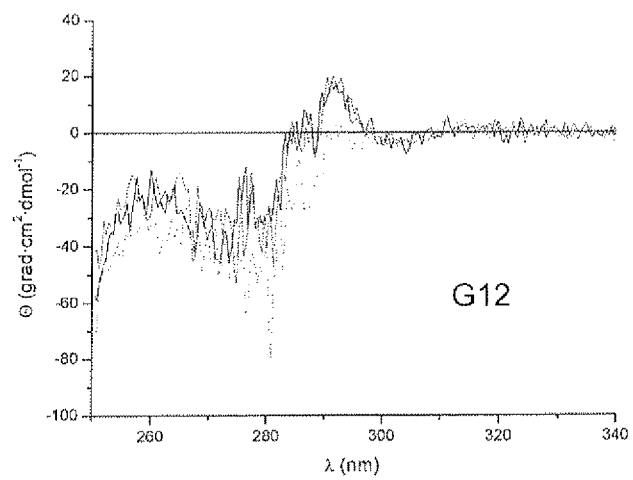
B
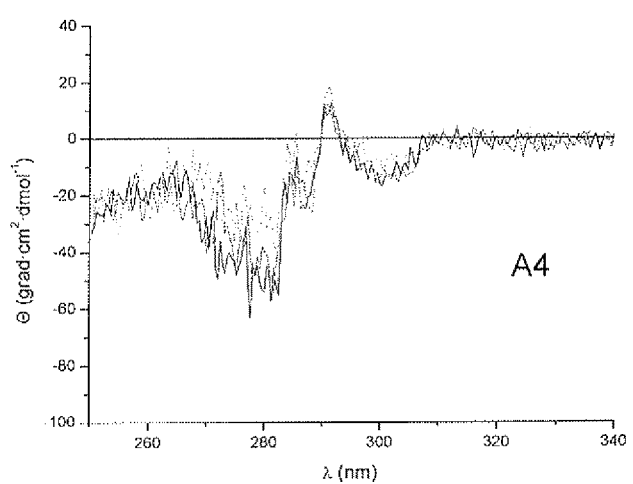
C
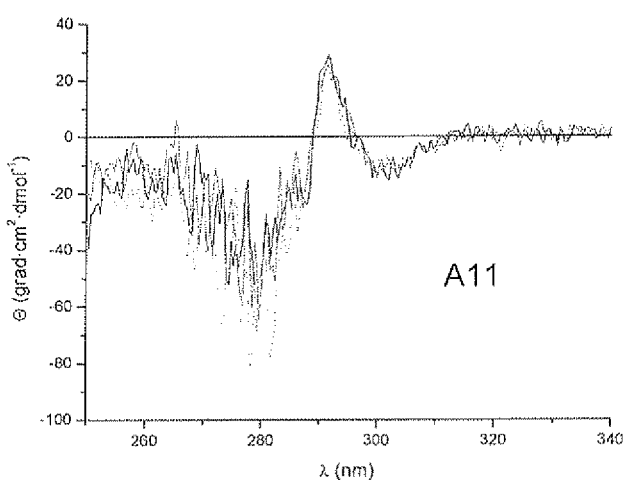
Figure 11.

A
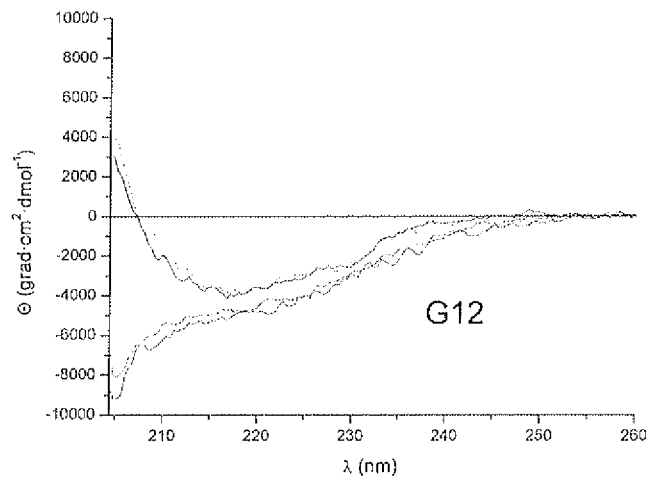
B
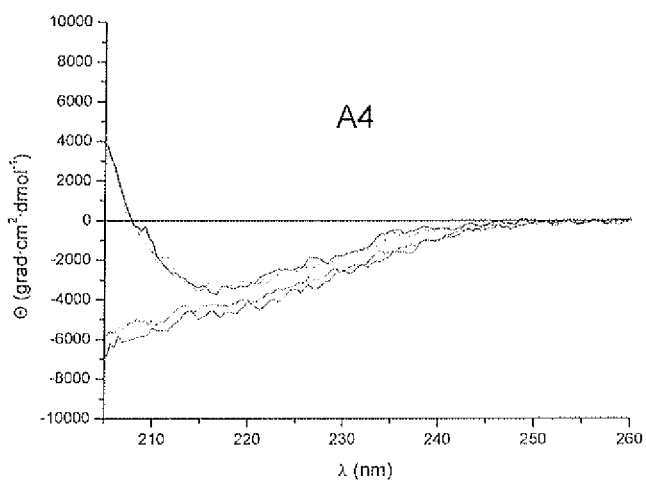
C
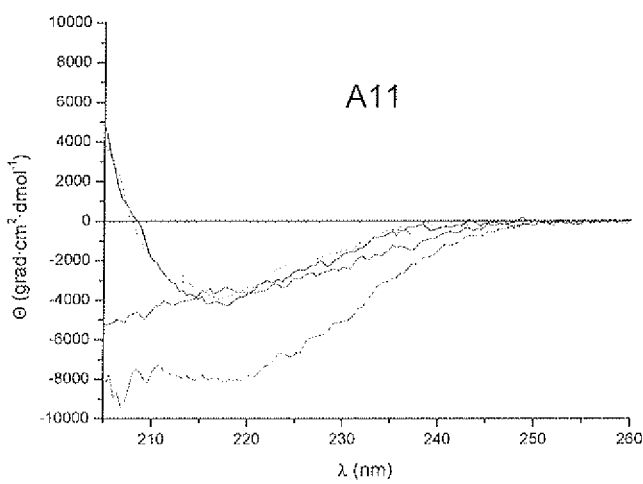
Figure 13.

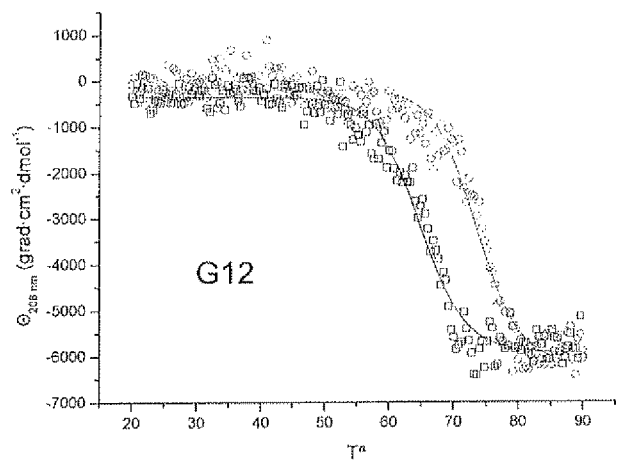
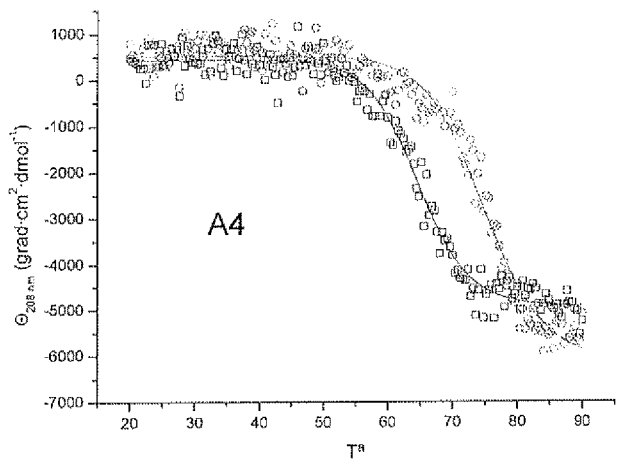
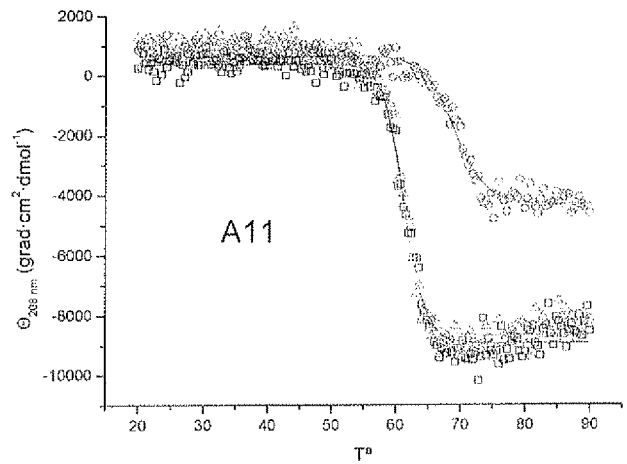
Figure 14.

CL-ELISA data
scFV's + Neoglycoproteins

Raw data
Relative luminescence units (RLU)

| | Cys-BSA | Galα(1,3)Galβ(1,4)GlcNAcβ | Galβ(1,4)Glcβ | Galα(1,6)Galα(1,2)Galβ | Galα(1,3)Galβ(1,4)Glcβ | Galα(1,6)Galβ-BSA | Galα(1,4)Galβ | Galα(1,3)Galβ | Galα(1,2)Galβ | Galα |
|---|---|---|---|---|---|---|---|---|---|---|
| scFv G12 (4 µg/ml) | 6 | 950 | 5 | 8 | 8 | 866 | 6 | 6 | 1434 | 7 | 8 |
| scFv G12 (4 µg/ml) | 6 | 997 | 4 | 11 | 7 | 951 | 5 | 7 | 1494 | 7 | 8 |
| scFv A4 (4 µg/ml) | 5 | 462 | 6 | 9 | 5 | 450 | 4 | 5 | 436 | 6 | 8 |
| scFv A4 (4 µg/ml) | 6 | 444 | 6 | 11 | 7 | 497 | 10 | 10 | 466 | 13 | 14 |

Figure 16

DETECTION OF FREE AND PROTEIN-BOUND NON-HUMAN GAL-ALPHA(1-3)-GAL EPITOPE

CROSS-REFERENCE TO RELATED APPLICATIONS

This application is a national phase application under 35 U.S.C. § 371 of International Application No. PCT/EP2013/071367, filed Oct. 11, 2013, which in turn claims priority to European Application No. 12188179.1, filed Oct. 11, 2012, the entire content of each of which is incorporated herein by reference.

SEQUENCE LISTING

The instant application contains a Sequence Listing which has been submitted in ASCII format via EFS-Web and is hereby incorporated by reference in its entirety. Said ASCII copy is named Final_Sequence_listing.txt and is 14.921 bytes in size.

FIELD OF THE INVENTION

The present invention relates to the provision of antibody fragments capable of binding selectively to the Gal-α-(1→3)-Gal epitope. This epitope is often found on porcine tissue destined for human transplantation. The invention further relates to assay systems comprising these antibody fragments for use in testing transplantation tissue for possible rejection complications. The epitope is also found on biopharmaceuticals and on some infectious agents and accordingly the invention also provides assay systems for these applications.

BACKGROUND OF THE INVENTION

The immunological importance of the non-human Gal-α-(1→3)-Gal epitope was initially highlighted by its direct involvement in hyperacute rejection (HAR) of porcine organ xenografts. Xenotransplantation has been widely considered as a direct means of overcoming the critical shortage of human donor organs with porcine organs, in particular, being considered the most suitable. However, porcine tissue expresses a high proportion of the Gal-α-(1→3)-Gal epitope and elicits a vigorous anti-Gal-α-(1→3)-Gal antibody response following transplantation of porcine xenografts into humans. Undesirable immune responses to this epitope are also thought to be involved in the sub-optimal clinical outcomes after implantation of a cellular tissue matrices. Naturally-occurring human antibodies directed against the Gal-α-(1→3)-Gal epitope are widespread in man, comprising up to 3% of immunoglobulin (Ig) in human sera (mainly IgG2 subclass). Their induction by environmental stimuli, commensal bacteria and/or parasitic interaction has been proposed and they putatively exert a natural barrier function. As well as its involvement in HAR, the presence of this antigenic glycan moiety has also been attributed to an IgE-mediated allergic/hypersensitivity response observed in patients taking the recombinant monoclonal antibody preparation, Erbitux (Cetuximab). The levels of Gal-α-(1→3)-Gal epitope required to induce anaphylaxis remain undetermined and may be both product-specific and patient-dependent.

The production of recombinant antibodies and related biopharmaceuticals is now seen as a well-established and a routinely performed industrial process, as evidenced by the increase in biosimilar production plants over recent years. Control over glycosylation is a critical factor during recombinant therapeutic production because of its profound effect on protein function, allergenic and immunogenic properties, plasma clearance rates and efficacy. It is now accepted that specific glycan structures adversely affect the safety of these recombinant products. The mammalian cell lines utilised for production, most commonly murine derived cell lines SP2/0 and NS0 or Chinese hamster ovary cells (CHO) permit 'human-like' glycosylation to occur. However, these cell line systems possess the molecular machinery to incorporate non-human glycan structures, including the Gal-α-(1→3)-Gal and N-glycolylneuraminic acid (Neu5Gc) moieties, into the target protein making them immunogenic in humans. The ability of the CHO system to synthesise the Gal-α-(1→3)-Gal glycan has only recently been reported, contrary to previously accepted reports detailing the lack of the biosynthetic machinery to synthesize glycoproteins with Gal-α-(1→3)-Gal moieties. Bosques et at demonstrated both the ability of CHO cells to synthesise the Gal-α-(1→3)-Gal moiety and its presence on the commercial therapeutic protein, Abatacept (Orencia), a CHO-generated antibody fusion protein. However, the level of Gal-α-(1→3)-Gal detected on proteins produced in the CHO system were lower than those typically observed on products derived from murine cell lines (Bosques et al., 2010). With the identification of Gal-α-(1→3)-Gal on recombinant proteins currently on the market, there is a need for convenient and rapid analytical approaches to monitor and quantify the levels of Gal-α-(1→3)-Gal on existing and future recombinant therapeutics for human use.

Furthermore, the possibility of exploiting the Gal-α-(1→3)-Gal epitope/natural human antibody system to improve the efficacy of autologous vaccines is gaining increased attention recently and this will also demand convenient assay tools.

The combination of high-performance liquid chromatography (HPLC) coupled with mass spectrometry (MS) and endoglycosidase digestion provides sufficient resolution and sensitivity for the identification and measurement of N-glycans. In addition, capillary electrophoresis with laser-induced fluorescence detection (CE-LIF) has also been used for profiling of the fluorescently labelled N-glycans because of its throughput and high-resolution separation capability. There have also been reports of structural analysis of N-glycans of a number of glycoproteins and recombinant mAbs by CE-LIF after fluorescent labelling with 8-aminopyren-1, 3,6-trisulfonate (APTS). The problem with these methods is that they are cumbersome, time-consuming to perform and require specialist equipment and instrumental expertise.

A number of pathogenic organisms also express the Gal-α-(1→3)-Gal epitope, such as *Trypanosoma cruzia*, the causitive agent of Chagas' disease, American *Leishmania, Colletotrichum*, which is a fungal plant pathogen and *Neisseria meningitides*. Thus, an anti-Gal-α-(1→3)-Gal antibody or fragment could be used either in diagnosis of these diseases or in their therapy. This epitope has also been implicated in anaphylactic reactions to oligosaccharides found in red meat and thus the antibodies of the invention could find use in the prevention or prediction of such responses.

Specific binding assays provide robust analytical platforms once high affinity and specific binding agents are available for the analytes. Lectins are the most widely used affinity reagents for carbohydrates, with less reliance on antibodies, due to limited availability of high quality antibodies. Two lectins are commonly used for the detection of the Gal-α-(1→3)-Gal motif. *Griffonia simplicifolia* I isolectin B4 (GS-I-B4) detects terminal Gal-α-1-R (alpha-galactosyl residues, termed alpha-Gal or αGal) epitopes, but cannot distinguish between structures in which the terminal galactose is linked to different carbon atoms in the penultimate galactose on the carbohydrate chain (e.g. Gal-α-1>2, Gal-α-1→3 or Gal-α-1→4). Binding of GS 1-B4 may also depend on whether the Gal-α-(1→3)-Gal is on a cell surface or on an isolated glycoprotein, as has been reported for a number of glycan recognition molecules. *Marasmius oreades* agglutinin (MOA) is also known to bind with Gal-α-1-R terminated structures. Although a number of anti-Gal-α-(1→3)-Gal antibodies have been described, only a small number are commercially available, including a polyclonal antibody raised in baboon and the M86 mouse IgM monoclonal antibody which have found limited application to date.

There are still significant challenges in the generation of high quality antibodies targeting carbohydrate motifs because of their low immunogenicity. Yet, human serum and the serum of many animals contain a wide range of natural anti-carbohydrate antibodies. Engineered single chain antibody fragment (scFv) libraries generated from immunoglobulin cDNA, whether from naive or immune-challenged host systems, may provide access to these antibodies. Chickens, like humans, do not produce the Gal-α-(1→3)-Gal epitope and hence develop a strong immune response on exposure to this motif. The generation of chicken antibody libraries has been shown to be simpler than libraries from mammalian species, due to the peculiar mechanism of immunoglobulin gene diversification in birds. Chickens possess single functional immunoglobulin heavy chain variable region ($V_H$) and light chain variable region ($V_L$) genes, with diversity created by the high frequency gene conversion mechanism operating continuously during B cell proliferation in the bursa. Here we describe the generation of a Gal-α-(1→3)-Gal targeted phage displayed-scFv library and isolation of chicken scFv antibody fragments directed against this epitope. These scFvs were shown to be highly specific for the detection of the Gal-α-(1→3)-Gal motif when tested in direct ELISA format against a panel of related neoglycoconjugates (NGCs). The antibody fragments in of the present invention were demonstrated to have high affinity and specificity for the Gal-α-(1→3)-Gal motif and have thus proved to be more effective and therefore much more commercially useful than previously known anti-Gal-α-(1→3)-Gal antibodies. The scFvs of the invention were also used in competitive ELISA format, where they allowed the concentration of Gal-α-(1→3)-Gal to be determined in free solution and when present on the surface of a glycoprotein. To our knowledge, this is the first report of a panel of engineered scFvs against the non-human carbohydrate Gal-α-(1→3)-Gal motif, and most importantly the first report of a convenient competitive ELISA for detection of this motif on glycoproteins.

OBJECT TO THE INVENTION

The non-human Gal-α-(1→3)-Gal carbohydrate epitope has recently been reported to be present on a number of recombinant therapeutic proteins. This antigenic carbohydrate epitope is known to be the primary contributing factor in hyperacute rejection of porcine organ xenograft, due to the existence of natural antibodies against this epitope in man. Though the number of epitopes on recombinant glycoproteins may be low when compared directly to whole tissue, the immunological response of circulating anti-Gal-α-R immunoglobulins can still induce anaphylaxis. Therefore, it is an object of the invention to provide antibody fragments for the detection, monitoring and quantification of the levels of this epitope in biopharmaceuticals, and recombinant therapeutics produced in recombinant mammalian systems. A particular object is to provide antibody fragments with high affinity for the Gal-α-(1→3)-Gal epitope. A further object is to provide an assay system for the detection and measurement of the Gal-α-(1→3)-GAL epitope on recombinant proteins or in tissues destined for transplantation. Such an assay system should be rapid and convenient to carry out. A further object is to provide a point-of-care assay system. A further object is to provide an assay tool to enable the improvement of the efficacy of autologous vaccines.

SUMMARY OF THE INVENTION

According to the present invention there is provided an antibody having a variable light chain sequence and a variable heavy chain sequence, the variable light chain sequence comprising at least two of the sequences: at least two of the sequences:—

$$SGG-x^1-x^2-x^3-x^4-x^5-x^6-x^7-Y(SEQ\ ID\ NO:5) \quad (1)$$

wherein $x^1$ is N or G or absent; $x^2$ is S or absent; $x^3$ is Y or absent; $x^4$ is GG or absent; $x^5$ is S or absent; $x^6$ is Y or G or absent, and $x^7$ is N, H or Y, $$SN-x^8-x^9-RPS(SEQ\ ID\ NO:6) \quad (2)$$

wherein $x^8$ is N or D and x9 is K, N or Q, or $$G-x^{10}-YD-x^{11}-x^{12}-x^{13}-x^{14}-Y-x^{15}-Gx^{16}(SEQ\ ID\ NO:7) \quad (3)$$

wherein $x^{10}$ is A, T or S; $x^{11}$ is S or N; $x^{12}$ is S or absent, $x^{13}$ is N or absent $x^{14}$ is T or S, $x^{15}$ is V or A, and $x^{16}$ is V or I; or (4) sequences which have at least 80% homology with any of the sequences (1) to (3);
the variable heavy chain sequence comprising at least two of the sequences:—

$$GFTFSSYSMQ(SEQ\ ID\ NO:8) \quad (5)$$

$$x^{17}-SD-x^{18}-YTYFGPAVKG(SEQ\ ID\ NO:9) \quad (6)$$

wherein $x^{17}$ is Y or N, and $x^{18}$ is S or R, $$S-x^{19}-D-x^{20}-GCTHPWCSADNI-x^{21}-A(SEQ\ ID\ NO:10) \quad (7)$$

wherein $x^{19}$ is A or G, $x^{20}$ is TIY or SGN, and $x^{21}$ is D or N, or (8) sequences which have at least 80% homology with any of the sequences (5) to (6).

The antibody may comprise all of the sequences (1) to (3) or (5) to (7) or sequences with at least 80% homology with any of these sequences.

The antibody may further comprise a linker sequence of the formula:—

$$GQSSRSS-x^{22}-GGG\ SSGGGGS(linker\ sequence) \\ (SEQ\ ID\ NO:11), \quad (9)$$

wherein $x^{22}$ is S or absent,
or a sequence having at least 80% homology to the sequence (9).

The scFv antibody fragment may have the generic sequence:

(SEQ ID NO: 1)
QAALTQPSSVS[T/A]NPGGTVKITCSGG[N/G/-][S/-][Y/-][G/-]

[G/-][S/-][G/Y][N/H/Y]YGWYQQKSPGSAPVTVIYSN[N/D][K/

Q/N]RPS[D/G]IPSRFSGS[T/K]S[G/D]ST[A/G/S]TLTITGVQ[V/

A]DDEAVY[F/Y]CG[A/S/T]YD[N/S][S/-][N/-][T/S]Y[V/A]G

-continued

[V/I]FGAGT[T/A]LTVLGQSSRSS[S/-]GGGSSGGGGSAVTLDESGGG

LQTPGG[G/A]LSLVCKASGFTFSSYSMQWVRQ[T/A]PGKGLEFVAGIG

[Y/N]SD[S/R]YTYFGPAVKGRATISRDNGQ[N/S]T[V/L]RLQLNNLR

AEDTATY[Y/F]CARS[A/G]D[T/S][I/G][Y/N]GCTHPWCSADNI

[D/N]AWGHGTEVIVSSTSGQAGQ wherein [ ] indicates a variable amino acid and indicates a deletion of an amino acid. Thus where [ ] is indicated, the amino acid may be any of those listed in the brackets and where a dash is indicated, the amino acid may be deleted.

The amino acids are abbreviated as follows:—

| Abbreviation | 1 letter abbrev | Amino acid name |
|---|---|---|
| Ala | A | Alanine |
| Arg | R | Arginine |
| Asn | N | Asparagine |
| Asp | D | Aspartic acid (Aspartate) |
| Cys | C | Cysteine |
| Gln | Q | Glutamine |
| Glu | E | Glutamic acid (Glutamate) |
| Gly | G | Glycine |
| His | H | Histidine |
| Ile | I | Isoleucine |
| Leu | L | Leucine |
| Lys | K | Lysine |
| Met | M | Methionine |
| Phe | F | Phenylalanine |
| Pro | P | Proline |
| Ser | S | Serine |
| Thr | T | Threonine |
| Trp | W | Tryptophan |
| Tyr | Y | Tyrosine |
| Val | V | Valine |
| Asx | B | Aspartic acid or Asparagine |
| Glx | Z | Glutamine or Glutamic acid |

The antibody may be a monoclonal antibody, an scFv fragment or an Fab fragment. The scFv antibody fragment may have the sequence of any one of sequence Ids. Nos 2, 3 or 4, as defined herein. Particularly preferred is Sequence ID No. 2.

The terms "homology" or percent "identity," in the context of two or more polypeptide sequences, refer to two or more sequences or subsequences that are the same or have a specified percentage of amino acid residues that are the same (i.e., at least 80%, at least 85%, at least 90%, 91%, 92%, 93%, 94%, 95%, 96%, 97%, 98%, 99%, or higher identity over a specified region, when compared and aligned for maximum correspondence over a comparison window or designated region as measured by computer program, or by manual alignment and visual inspection. Such sequences are then said to be "substantially identical" or 'substantially homologous'. The definition also includes sequences that have deletions and/or additions, as well as those that have substitutions. The preferred algorithms can account for gaps and the like. Preferably, identity exists over a region that is at least about 5 amino acids in length, or more preferably over a region that is 10-15 amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence homologies for the test sequences relative to the reference sequence, based on the program parameters. The invention also provides an assay kit for the determination of the presence or the quantification of a Gal-α-(1→3)-Gal motif in tissues or cells or on proteins, comprising at least one antibody as defined above. The assay may be any form of immunoassay, including but not limited to an an ELISA assay, a competitive or inhibition ELISA, a sandwich ELISA assay, a micro-array based assay, a functionalised nanoparticle assay, other rapid assay platform such as QDots, F1 tags and electro sensors, an immunohistochemistry assay, or a flow cytometry assay. The antibodies of the invention may be employed within assay formats, surface presented be it on array, nanoparticle or membrane, and/or presented in suspension form. The antibodies of the invention may also be used in conjunction with other antibodies in sandwich ELISAs for the detection of specific glycoproteins. The antibodies may function as printed components on microarrays.

In another aspect the invention provides a method of determining the presence of, or of quantifying the amount of a Gal-α-(1→3)-Gal motif in tissues or cells or on proteins, comprising determining the degree of binding of an antibody or antibody fragment, as defined above, to the tissue, cell or protein.

The antibodies of the present invention may also be used as therapeutic agents against infectious disease and diseased condition states which occur via interaction of the Gal-α-(1→3)-Gal motif, in the determination of Gal-α-(1→3)-Gal specific antibodies circulating in human serum in a competition format, for disease detection and as a monitoring assay for anaphylaxis, as a Gal-α-(1→3)-Gal motif staining and detection agent for immuno staining (IHC, IFC, FACs etc) and visualization, as an affinity reagent to purify and isolate Gal-α-(1→3)-Gal motif bearing molecules from both natural and recombinant biologic preparations, as an affinity reagent to purify and isolate Gal-α-(1→3)-Gal motif bearing organisms for pathogen control, as an affinity reagent for testing in place for the assessment and monitoring of the Gal-α-(1→3)-Gal motif during the production of therapeutic glycoprotein products from mammalian cell systems.

In a still further aspect the invention provides a pharmaceutical composition comprising an antibody fragment as defined herein together with a pharmaceutically acceptable carrier or excipient.

The antibodies are also suitable for assays for the detection of the target glycan when linked to a protein and also in free form, whether naturally released or specifically released from the glycoprotein by enzyme treatment.

The antibodies may also be used for the removal of glycoproteins carrying the target motif from a mixture of glycoforms, as for example in biopharmaceutical production where only a small proportion of the molecules would be expected to carry the motif.

BRIEF DESCRIPTION OF THE DRAWINGS

FIG. 9: Alignment of fused light chain and heavy chain amino acid sequences of the selected scFv fragments A4, A11 and G12 as expressed as soluble protein and presented for recognition of the epitope (SEQ ID NOS. 2-4).

FIG. 10: Generic antibody sequence (SEQ ID NO. 1) showing complementarity determining regions (SEQ ID NOS. 5-10), and linker sequence (SEQ ID NO. 11).

FIG. 11. Near UV CD spectra, expressed as molar ellipticity per residue recorded for scFvs G12 (A), A4 (B) and A11 (C) in the absence (black) and presence of 4 mM melibiose (red) and Galα(1,3)Galβ1-OMe (green), in NaPi (10 mM)-NaCl (150 mM) pH 7.2 at 20° C. Samples were prepared by ultrafiltration.

FIG. 13. Far UV CD spectra, expressed as molar ellipticity per residue of scFvs G12 (A), A4 (B) and A11 (C) in the absence and presence of 4 mM Galα(1,3)Galb1-OMe in NaPi (10 mM)-NaCl (150 mM) pH 7.2. Pure scFv at 20° C. (black), pure scFv at 90° C. (red), scFv with sugar at 20° C. (green), scFv with sugar at 90° C. (blue). Samples of G12 and A11 were prepared by ultrafiltration and samples of A4 by dialysis.

FIG. 14. Denaturation profiles for scFvs G12 (A), A4 (B) and A11 (C). The continuous line corresponds to the fit of a sigmoidal function to the experimental data, using the equation mentioned in the text. Pure scFv (black), scFv+Galα (1,3)Galb1-OMe (red) and scFv+melibiose (green).

FIG. 16. Raw data for FIG. 15.

DETAILED DESCRIPTION OF THE DRAWINGS

Materials and Methods

Figure 1:
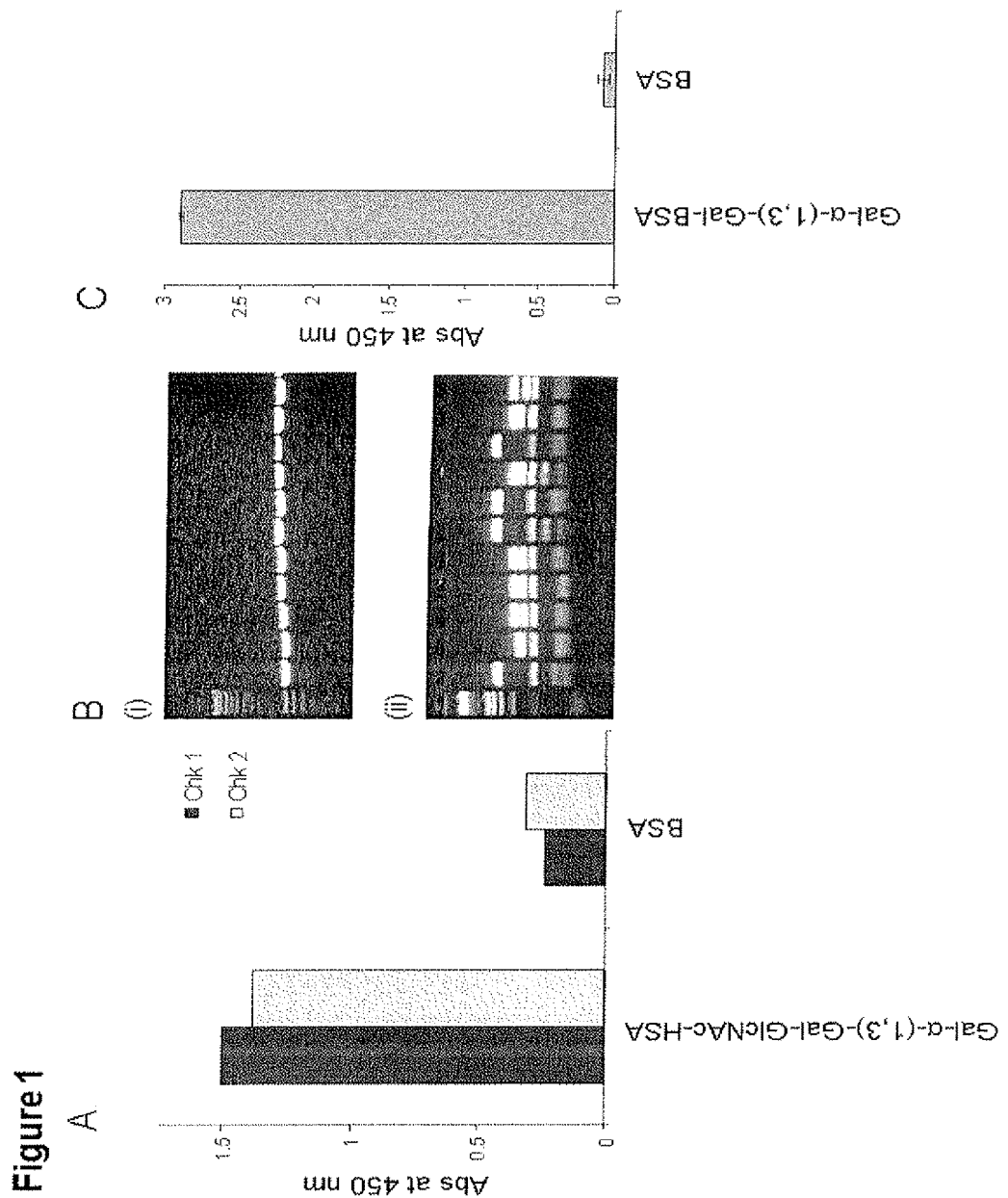
FIG. 1: (A) Chicken serum response to immunisation with Gal-α-(1→3)-Gal-BSA as determined by direct ELISA (Serum dilution 1:20,000). (B) Demonstration of the (i) insertion of the encoding scFv fragment and (ii) the diversity within this fragment across randomly selected clones examined by restriction digestion. (C) Binding to Gal-α-(1,3)-Gal-BSA of biopanning round 2 output phage particles

Chicken Immunization.

A pooled glycoconjugate preparation composing of human α-acid glycoprotein, porcine lactoferrin, honey bee phospholipase A2, Gal-α-(1→3)-Gal-BSA and soluble glycoprotein fraction taken from CHO cell media were combined at an equal ratio. Adult male Leghorn chickens were immunized subcutaneously, at 21-day intervals, with 50 μg of the glycoconjugate preparation in a total volume of 400 μl. The first dose was prepared with complete Freund's adjuvant, and three subsequent doses were administered with incomplete Freund's adjuvant. Serum anti-Gal-α-(1→3)-Gal response was evaluated, seven days after the third inoculation, via direct enzyme-linked immunosorbent assay (ELISA) analysis, FIG. 1a. Briefly, 96-well immunoassay plates (Maxisorp; Nunc) were coated overnight at 4° C. with 100 μl/well Gal-α-(1→3)-Gal-GlcNAc-HSA at 10 μg/ml. Wells were then blocked for 1 hour at 37° C. with 0.5% BSA-PBS (PBS-B). Serum samples were serially diluted in PBS-B containing 0.1% Tween 20 (PBS-BT) and added to the plates 100 μl/well. Plates were then incubated at 37° C. for 1 hour, washed 10 times with PBS-0.1% Tween 20 (PBS-T), and probed for 1 hour at 37° C. with horseradish peroxidase (HRP)-conjugated anti-chicken IgG antibody (Pierce) in PBS-BT. After washing with PBS-T, the wells were developed with 100 μl/well HRP substrate, tetramethylbenzidine (DAKO), and reactions were stopped with 100 μl/well 1 M $H_2SO_4$. All analyses were performed in triplicate.

Chicken scFv Library Generation.

Library generation and phage display was performed using the protocols as described by Andris-Widhopf et al. (Andris-Widhopf et al., 2000). Briefly, total RNA was isolated from the spleen and bone marrow of one femur from each chicken (TRIzol Reagent, Invitrogen) and first-strand cDNA synthesised (Superscript II, Invitrogen Inc) both as per manufacturers protocol. The scFv library was generated using a two step approach with initial amplification of heavy and light chains, followed by overlap extension PCR, with the scFv cDNA products introduced into the pComb3 phagmid system via ligation (Andris-Widhopf et al., 2000) and subsequently transformed into electrocompetent E. coli XL1-Blue cells [F' proAB lacIqZΔH15 Tn10 (Tetr)] (Stratagene). All amplification oligonucleotides were as described by Andris-Widhopf et al. Total library size were estimated by antibiotic resistance plate counting on Luria-Bertani (LB) agar containing 100 μg/ml carbenicillin (Sigma). scFv insertion was validated by colony PCR and library sequence diversity assessed using endonuclease BstNI digestion of PCR products (Promega) and visualised by agarose gel electrophoresis, FIG. 1b. The completed library preparations were propagated in XL1-Blue cells, and held as glycerol stocks.

Rescue of scFv-Displaying Phage.

To rescue scFv-displaying phage, 50 ml super broth (SB) supplemented with 2% glucose, 50 μg/ml ampicillin and 10 μg/ml tetracycline was inoculated with approximately $2 \times 10^9$ cells from the glycerol stock library. The culture was then incubated with rotation at 37° C. until an $OD_{600}$ of 0.5, was reached. At this point the culture is co-infected with $10^{12}$ colony-forming unit of VCSM13 helper phage (Stratagene) and increased to a volume of 200 ml with SB. After 90 minutes incubation, 50 µg/ml kanamycin was added and incubation 30° C. overnight carried out. Phage particles were purified and concentrated from the liquid medium by PEG/NaCl precipitation (Andris-Widhopf et al., 2000), and resuspended in 1% OVA-PBS (PBS-O).

Selection by Biopanning of scFv Phage Libraries Against Gal-α-(1→3)-Gal-BSA.

Biopanning against Gal-α-(1→3)-Gal-BSA was performed using Maxisorp immunotubes (Nunc). Briefly, tubes were coated overnight at 4° C. with 1 ml of 10 µg/ml Gal-α-(1→3)-Gal-BSA (Dextra, UK) and then blocked with PBS-B. $1×10^{11}$-$10^{12}$ scFv-displaying phage suspended in PBS-0 were then added and mixed by rotation for 1 hour at room temperature. Follow by repeated washing with PBST, and then with PBS only. Bound phage were eluted with the addition of 1 ml 100 mM glycine-HCl, pH 2.2 for 10 min. Eluted phage were neutralized using 500'11 of 1M Tris-HCl, pH 8.8. Propagation of eluted phage and further manipulations were then carried out, as previously described (Andris-Widhopf et al., 2000). Three rounds of panning were performed, with increasing selection stringency mediated by a progressive increase in washing steps from 10 in pan 1 to 15 in pan 2 and 3.

ELISA Analysis of the scFv-Phage Population Pool after Each Round of Biopanning.

Eluted scFv-displaying phage suspensions from each round of panning were assessed for Gal-α-(1→3)-Gal binding by direct ELISA analysis. Immunoassay plates (Maxisorp, Nunc) were coated and blocked as described above, and threefold dilution of phage-scFv preparations (in PBS-BT) added to the wells. BSA and HSA were included as negative references. After 1 hour of incubation at 37° C., plates were washed with three times with PBS-T and probed with HRP-conjugated anti-M13 antibody (GE Healthcare) in PBS-BT for 1 hour at 37° C. After extensive washing with distilled water, the wells were developed as described above.

Single scFv-Phage Clones and Direct ELISA Analysis.

Ninety six random clones were picked from output plates from rounds 2 and 3 of panning and cultured in deep-well plates in super broth (SB) in the presence of 100 µg/ml carbenicillin for 6 hours at 37° C., 300 rpm. Cultures were then induced with 2 mM IPTG and grown overnight. Cells were pelleted by centrifugation at 2,500 g for 15 min at 4° C., and supernatants removed and stored at 4° C. Periplasmic scFv was liberated by resuspending the cell pellets in 100 µl of PBS and two rounds of freeze-thawing at −80° C. and 37° C. Plates were then centrifuged again as above, and supernatants were removed and added to their respective culture supernatant. Direct ELISA analysis of binding of single scFv-phage to Gal-α-(1→3)-Gal-BSA was then performed as described previously using HRP-conjugated anti-M13 antibody (GE Healthcare) in PBS-BT for 1 hour at 37° C. After extensive washing with distilled water, the wells were incubated with 100 µl/well HRP substrate (DAKO), and reactions were stopped with 1M $H_2SO_4$ as detailed previously.

Establishment of Individual scFv Clones for Stable Expression.

Colonies selected based upon observed binding to Gal-α-(1→3)-Gal-BSA were used to perform phagemid purifications (NucleoBond, Macherey-Nagel). The resulting plasmid preparations were transformed by electroporation into E. coli strain TOP 10F' (Invitrogen). An aliquot of each transformation was plated on LB carbenicillin agar to provide single colonies, permitting the testing of single-clone scFv properties.

Expression and Purification of Soluble scFv.

Colonies were cultured overnight in 5 ml SB containing 50 µg/ml carbenicillin (37° C., 250 rpm shaking). 50 µl of each clone culture was then added to 50 ml SB (50 µg/ml carbenicillin and 20 mM $MgCl_2$), and scFv production induced with the addition of 2 mM IPTG and cultured overnight. To isolate soluble antibody, the bacterial cells were pelleted by centrifugation and resuspended in equilibration buffer (50 mM $NaH_2PO_4$, 300 mM NaCl, 10 mM $C_3H_4N_2$, pH 8.0) containing 20 mM phenylmethylsulfonyl fluoride. Periplasmic scFv was then liberated by sonication and cell debris removed by centrifugation, the supernatant was filtered through a 0.22 µm syringe filter. Soluble scFv antibodies were purified by nickel chelation chromatography (Ni-NTA Superflow, Qiagen). For large scale production, culture volumes were increased to liter scale, with purification performed using an AKTA purifier FPLC (GE Healthcare) under nave conditions using HisTrap HP 1-ml (GE Healthcare) using ten column washes and a linear gradient up to 250 mM $C_3H_4N_2$ for all elutions. Purified samples were dialysed against PBS and concentrated by membrane filtration (5 kDa filtration columns; Vivascience). Protein concentration on final products was estimated by BCA assay (Pierce). Purified scFv were stored at a concentration of 1 mg/ml at 4° C.

DNA Sequencing of Single scFv Clones.

Plasmid DNA was isolated from the bacterial pellets as above for expression and purification of soluble scFv. Multiple read sequencing reactions were performed for both strands of the complete scFv inserts (Eurofins MWG Operon). Multiple sequence alignment, translation and recognition of CDRs was performed using BLAST (ncbi.nlm.nih.gov/BLAST), ClustalW2 from EBI (ebi.ac.uk/Tools/msa/) and the CDR repository held at bioinf.org.uk/abs.

Evaluation of Purified scFv by ELISA.

Prior to analysis a sub-saturating concentration of scFv was determined by testing a gradient of scFv concentrations against 10 ug/ml Gal-α-(1→3)-Gal-BSA. A concentration of 4 ug/ml was determined to be optimal and was applied throughout further testing. Direct ELISA analysis of the specificity of purified scFv was assessed using a panel of 13 NGCs comprising Gal-α-(1→3)-Gal-BSA, Gal-α-(1→3)-Gal-β-(1→4)-GlcNAc-HSA, Gal-α-1-O-spacer-ITC, Gal-β-1-O-spacer-ITC, Gal-α-(1>2)-Gal-BSA, Gal-β-(1→4)-Gal-BSA, β-Xyl-BSA, Fuc-α-4AP-BSA, Fuc-β-4AP-BSA, Neu5Ac-4AP-BSA, GlcNAc-BSA, Lac-β-4AP-BSA, LacNAc-BSA and two negative controls; HSA and BSA. ELISA performed as described with the exception of HRP-conjugated anti-HA antibody (Roche) in PBS-BT for 1 hour at 37° C. as the secondary antibody. After extensive washing with distilled water, the wells were incubated with 100 µl/well HRP substrate (DAKO), and reactions were stopped with 1M $H_2SO_4$. Biotinylated GS-I-B4 lectin (Ey Laboratories Inc, San Mateo, Calif., USA) and α-Gal Epitope (Galα1-3Galβ1-4GlcNAc-R), mAb (M86) (Enzo Life Sciences, Inc.) were used as control references for assay assessment. Secondary antibodies used were streptavidin-conjugated HRP (Thermo Fisher Scientific) and a polyclonal rabbit anti-mouse Ig HRP (P 0260, Dako).

Development of scFv-Based Competitive ELISAs for Gal-α-(1,3)-Gal.

Each scFv was evaluated in a competitive ELISA format using free Gal-α-(1,3)-Gal as standard. Microtitre plate wells were coated and blocked as previously described. Standard solutions were prepared in PBS (pH 7.2), ranging in concentration from 2 µg/ml (5.84 µM) to 20 mg/ml (58.4 mM). For the assay, 50 µl of each standard and buffer blank were added to designated wells in triplicate, followed by 50 µl of a sub-saturating concentration (1 µg/ml) of the appropriate scFv, giving a final standard concentration in the assay of 1 µg/ml (2.92 µM) to 10 mg/ml (29.2 mM). The plate was incubated for 1 hour at 37° C. with shaking After washing, bound scFv was detected as previously described. The ratios of the OD for each standard versus the OD given by the blank (B/Bo) were plotted versus standard concentration and standard curve plotted using SigmaPlot (v11, Systat Software Inc). The detection limits were determined as the concentration corresponding to the mean response for zero standard minus three times the standard deviation (SD). Inhibition of scFv by a panel of free sugars. scFv binding to Gal-α-(1→3)-Gal-BSA was determined against a panel of 21 free form sugars; D-Cellibiose, Melibiose, D-Raffinose, Lactulose, Palatinose, β-Gentibiose, D+ Trehalose, D+ Turanose, L– Fructose, D+ Glucose, Sucrose, Galacto-N-biose, 4β-Galactobiose, gal-α(1-3)-gal-β-(1-4)-gal, gal-α(1-3)-gal-β-(1-4)-glc, gal-α(1-3)-gal-β-(1-4)-gal-all-3)-gal, Laminarbiose, β1-4-D-Xylobiose, N-Acetyl-D-glucoseamine (GlcNAc), Galactose, N-Acetyl-D-lactosamine (LacNAc), (sourced from Sigma Aldrich and Dextra, UK). Inhibitions were performed by serial dilutions of free sugars and a sub-saturating concentration scFv added to each dilution and pre-incubated for 60 minutes at 37° C., prior to performing ELISA against Gal-α-(1→3)-Gal-BSA as used throughout. Inhibition concentration range used is provided in Table 1. The percent binding of the scFv was plotted against the free Gal-α-(1→3)-Gal-BSA concentration, and the 50% effective dose determined ($ED_{50}$; dose of free sugar causing 50% displacement of the scFv).

Results

Immune Response and Library Construction.

Analysis of the serum antibody response following immunization with Gal-α-(1→3)-Gal-BSA indicated a strong response to the target glycan motif in both immunized chickens (FIG. 1a). scFv libraries displayed on filamentous phage were generated from the combined RNA extracted from spleen and bone marrow of each chicken (Andris-Widhopf et al., 2000). Colony PCR revealed that all individual clones tested contained full size inserts and sequence diversity was confirmed by BstN1 restriction mapping of amplified products (FIG. 1b). The initial size of each library was estimated at approximately $5 \times 10^7$ transformants. Libraries were combined and panned as a single scFv-phage library.

Isolation of Anti-Gal-α-(1→3)-Gal scFv-Phage Particles.

Figure 2:
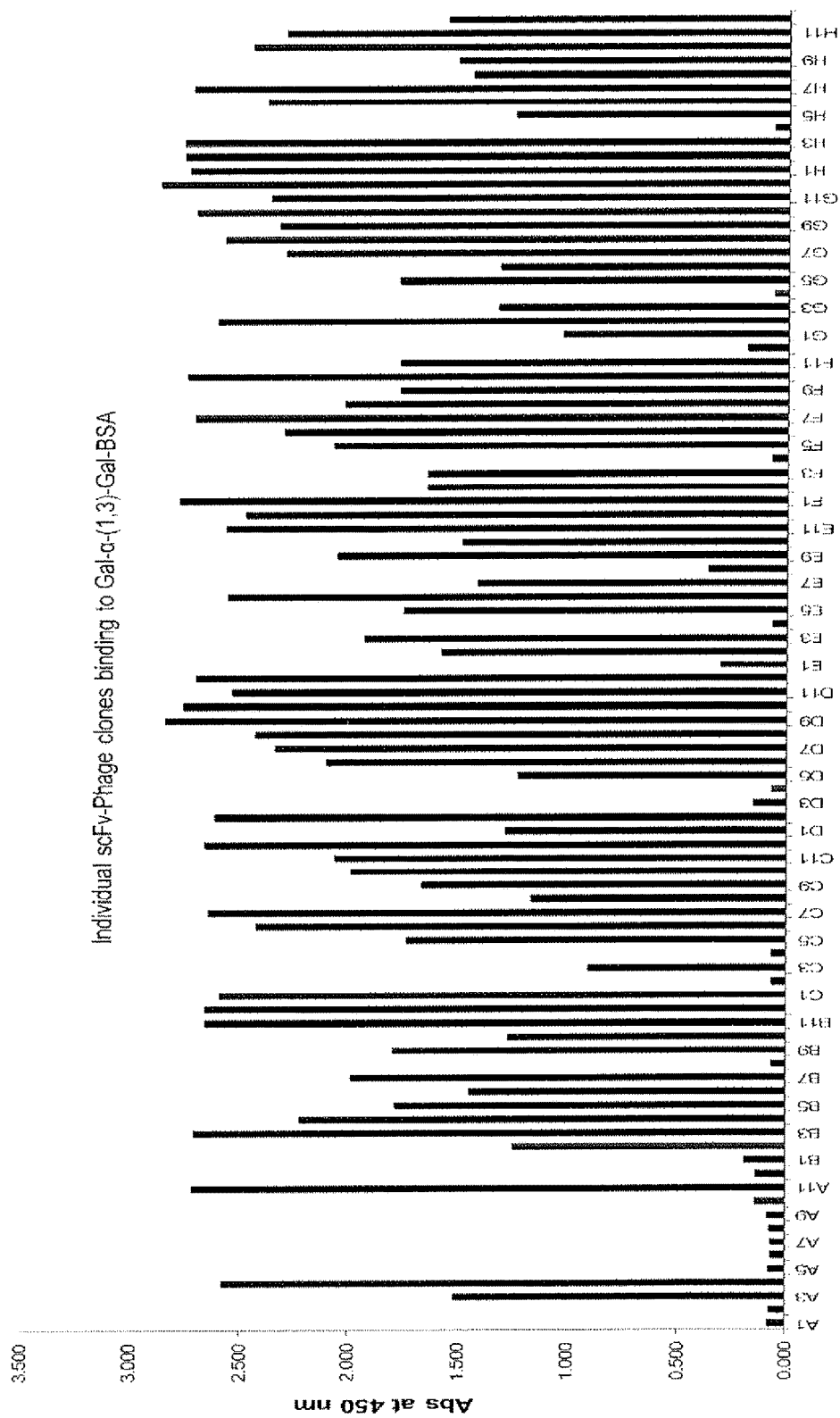
FIG. 2: Evaluation of 96 individual scFv-phage particles in direct ELISA against Gal-α-(1,3)-Gal-BSA. Indicated in blue are 6 scFv selected for further analysis from this population

Three rounds of biopanning were performed at room temperature against Gal-α-(1→3)-Gal-BSA under identical conditions and bound phage were eluted at low pH. Following the second round of panning, the presence of an enriched population of phage-displayed scFvs demonstrating binding to Gal-α-(1→3)-Gal-BSA was confirmed by direct ELISA (FIG. 1c). No further enrichment was observed after the third round. Minimal cross reactivity was observed against the carrier proteins, BSA or HSA. From the output phage of the second and third panning rounds, 96 individual phage clones were selected at random, cultured individually and analysed for specific binding activity. Of the 96 clones tested, 74 showed binding greater than 3 times background to the immobilised NGC (FIG. 2). Six of the higher binding clones (A4, A11, D9, F1, G12 and H3) were chosen for sequencing, and their encoding phagemids were transformed into TOP10 cells for inducible expression and generation of soluble scFv for downstream affinity purification.

Sequence Analysis of Isolated Clones.

Figure 3:
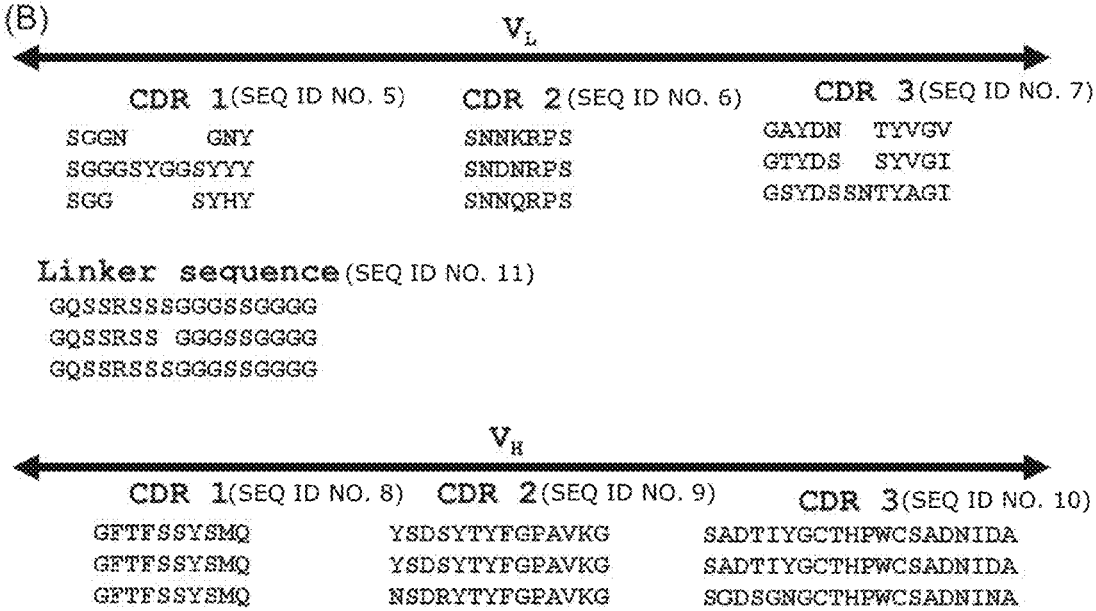
FIG. 3: Schematic alignment of CDRs from the VL and VH regions from 3 scFv sequenced clones demonstrating amino acid variants. (A) a generic schematic of a fused scFv and (B) alignment of scFv CDR. (LCDR 1=SEQ ID NO. 5, LCDR 2=SEQ ID NO. 6, LCDR 3=SEQ ID NO. 7, HCDR 1=SEQ ID NO. 8, HCDR 2=SEQ ID NO. 9, HCDR 3=SEQ ID NO. 10, Linker sequence=SEQ ID NO. 11).

Analysis of the nucleotide sequences of the $V_H$ and $V_L$ regions of the six scFvs demonstrated a high degree of consensus with germline chicken $V_H$ and $V_L$ regions. All clones exhibited considerable divergence in the $V_L$ complementarity determining region 1 (CDR1), CDR2 and CDR3 regions, with less variability in the $V_H$ region. Indeed the $V_H$ CDR 1 was conserved across all clones (FIG. 3). The sequence data suggests that the scFvs isolated were generated in an antigen-driven response, with particular reference to the $V_L$ regions, rather than being naive antibody sequences. Four unique sequences, representing clones A11/D9, F1/G12, H3 and A4, were identified (FIG. 3). Within the $V_L$ CDRs, single transitions occurred in a number of positions; (i) $V_L$ CDR1 where four codons were identified alternating from tyrosine (Y) to histidine (H) to asparagine (N) to lysine (K); (ii) in $V_L$ CDR2 where asparagine (N) to glutamine (Q) to lysine (K) occurred and (iii) $V_L$ CDR3 where threonine (T) to serine (S) to glycine (G) to alanine (A) was observed. In contrast, fewer polymorphic sites were observed across the $V_H$ regions, with A11/D9, H3 and A4 showing consensus across the CDR1, CDR2 and CDR3. F1/G12 differed from the other clones within the CDR3 region. Across the linker region two substitutions from the germline sequence were observed (serine (S) to glutamine (Q) and a glycine (G) to serine (S)) along with 2 serine (S) deletions shortening the linker region of A11/D9. Such observations of linker region alterations have been reported within similar libraries previously with no effect on library efficiency (Finlay et al., 2006).

Expression and Purification of Soluble scFv.

Figure 4:
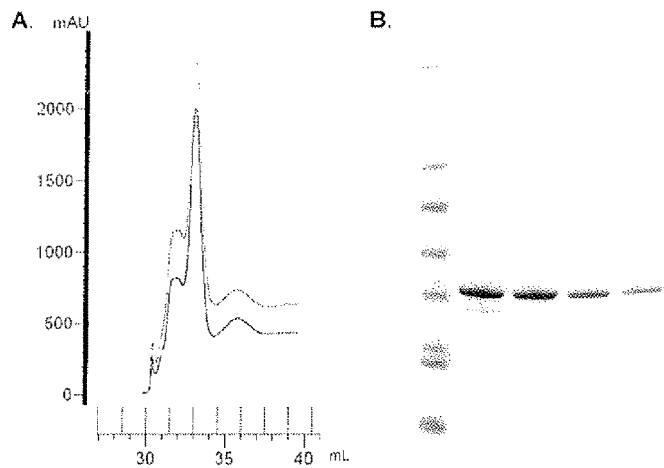
FIG. 4: (A) IMAC purification of soluble scFv from bacterial culture media. Image of FPLC output using a gradient elution, showing absorbance at 280 nm mAU (in blue), flow rate (mL min-1, in black), and gradient slope (in green). (B) SDS-PAGE on a 4-12% Bis-Tris NuPage gel of affinity-purified scFv fractions with Coomassie staining.

The four unique scFv clone sequences represented by A4, A11, G12 and H3, were carried forward for expression and purification of soluble scFv. Three were successfully expressed in bacterial culture (A4, A11 and G12), purified using Ni-NTA affinity chromatography, and purity confirmed by gel electrophoresis (FIG. 4). Yields of purified scFv were approximately 6.5 mg/L of bacterial culture medium. All purified scFv demonstrated stability at 4° C. for periods of up to 6 months in PBS. One clone, H3, failed to purify under both native and denatured conditions.

ScFv Specificity Evaluation by Direct ELISA.

Figure 5:
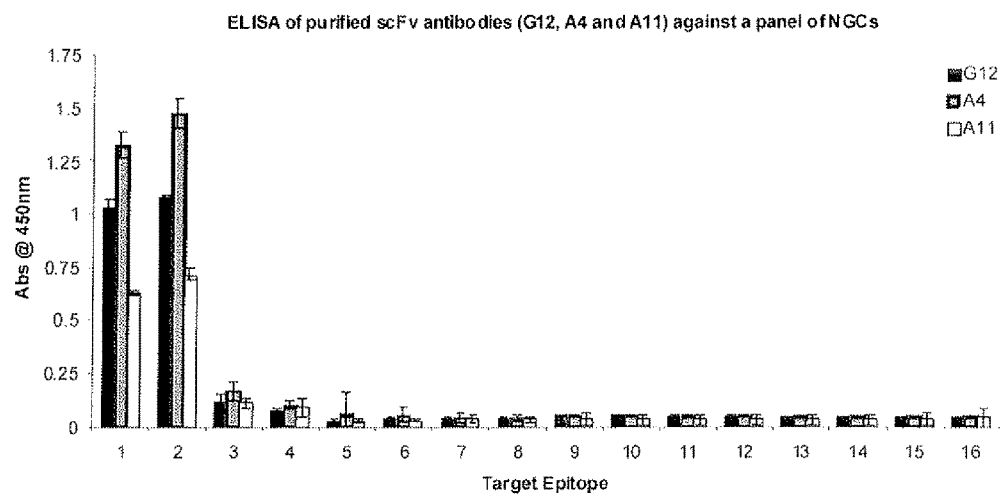
FIG. 5: Specificity profile of the three anti-Gal-α-(1→3)-Gal scFvs in direct ELISA. Wells were coated as follows: 1. Gal-α-(1→3)-Gal-BSA; 2. Gal-α-(1→3)-Gal-β-(1→4)-GlcNAc-HSA; 3. Gal-α-1-O-spacer-ITC-BSA; 4. Gal-β-1-O-spacer-ITC-BSA; 5. Gal-α-(1>2)-Gal-BSA; 6. Gal-β-(1→4)-Gal-BSA; 7. β-xyl-4AP-BSA; 8. Fuc-α-4AP-BSA; 9. Fuc-β-4AP-BSA; 10. Neu5Ac-4AP-BSA; 11. GlcNAc-BSA; 12. Lac-β-4AP-BSA; 13. LacNAc-BSA; 14. HSA, 15. BSA and 16. BSA-4AP. The error bars indicate the standard error of the mean of triplicate determinations.

The specificities of the purified scFv clones, A4, A11 and G12, were tested in a direct ELISA format against a range of Gal-α-R related neoglycoconjugates (NGCs). All three scFvs were specific for Gal-α-(1→3)-Gal-BSA, binding with slightly higher intensity to the Gal-α-(1→3)-Gal-β-(1→4)-GlcNAc-HSA compared to Gal-α-(1→3)-Gal-BSA (FIG. 5). This difference was likely due in part to the different molar substitution ratios of the glycan motif per molecule of albumin (16 and 23 for the disaccharide and trisaccharide NGCs, respectively), although the difference was not as great as expected suggesting that the scFvs having slightly greater affinity for the Gal-α-(1→3)-Gal disaccharide compared to the trisaccharide. The binding to the disaccharide and trisaccharide epitopes and not to the monosaccharide (Gal-α-1-O-spacer-ITC) or the Gal-α-(1>2)-Gal-BSA and Gal-α-(1→4)-Gal-BSA structures demonstrates that the α-(1→3) linkage is a requirement for binding. Similar binding specificity for Gal-α-(1→3)-Gal epitope was shown by all three scFvs tested, regardless of sequence diversity in the CDR regions (FIG. 3). No binding was observed to the other structures tested in the direct ELISA (Gal-α-1-O-spacer-ITC-BSA, Gal-β-1-O-spacer-ITC-BSA, Gal-α-(1>2)-Gal-BSA, Gal-α-(1→4)-Gal-BSA, D-xylose-β-BSA, Fuc-α-4AP-BSA, Fuc-β-4AP-BSA, Neu5Ac-4AP-BSA, GlcNAc-BSA, Lac-β-4AP-BSA, LacNAc-BSA) or to the carrier proteins, HSA, BSA and BSA-4AP. By comparison, the lectin GS-1-B4 showed significantly higher binding to the trisaccharide NGC compared to the disaccharide NGC and also bound to all Gal-α-1-R-containing NGCs (FIG. 5s), in consensus with previous reports. Therefore, the scFvs generated demonstrate a higher specificity than the GS-1-B4 lectin, for Gal-α-(1→3)-Gal. In parallel with the lectin GS-1-B4 and the monoclonal M86, all scFvs were able to detect the target motif on the natural glycoprotein, murine laminin, in direct ELISA (data not shown). Murine laminin is known to display the Gal-α-(1→3)-Gal motif.

Figure 6:
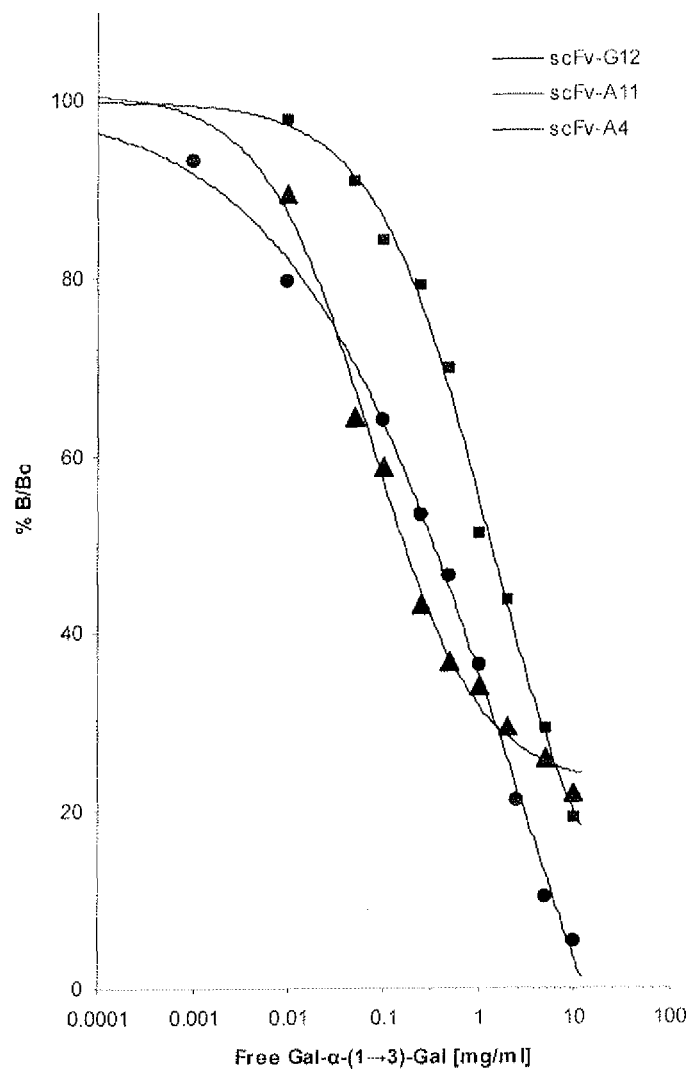
FIG. 6: Standard curves for competitive ELISA given by scFv clones G12, A4, and A11. Plates were coated with immobilized Gal-α-(1→3)-Gal-BSA [10 μg/ml] and incubated with 2.5 μg/ml of the scFvs in the presence of an increasing concentrations of free Gal-α-(1→3)-Gal. The error bars indicate the standard error of the mean of triplicate determinations.
Figure 8:
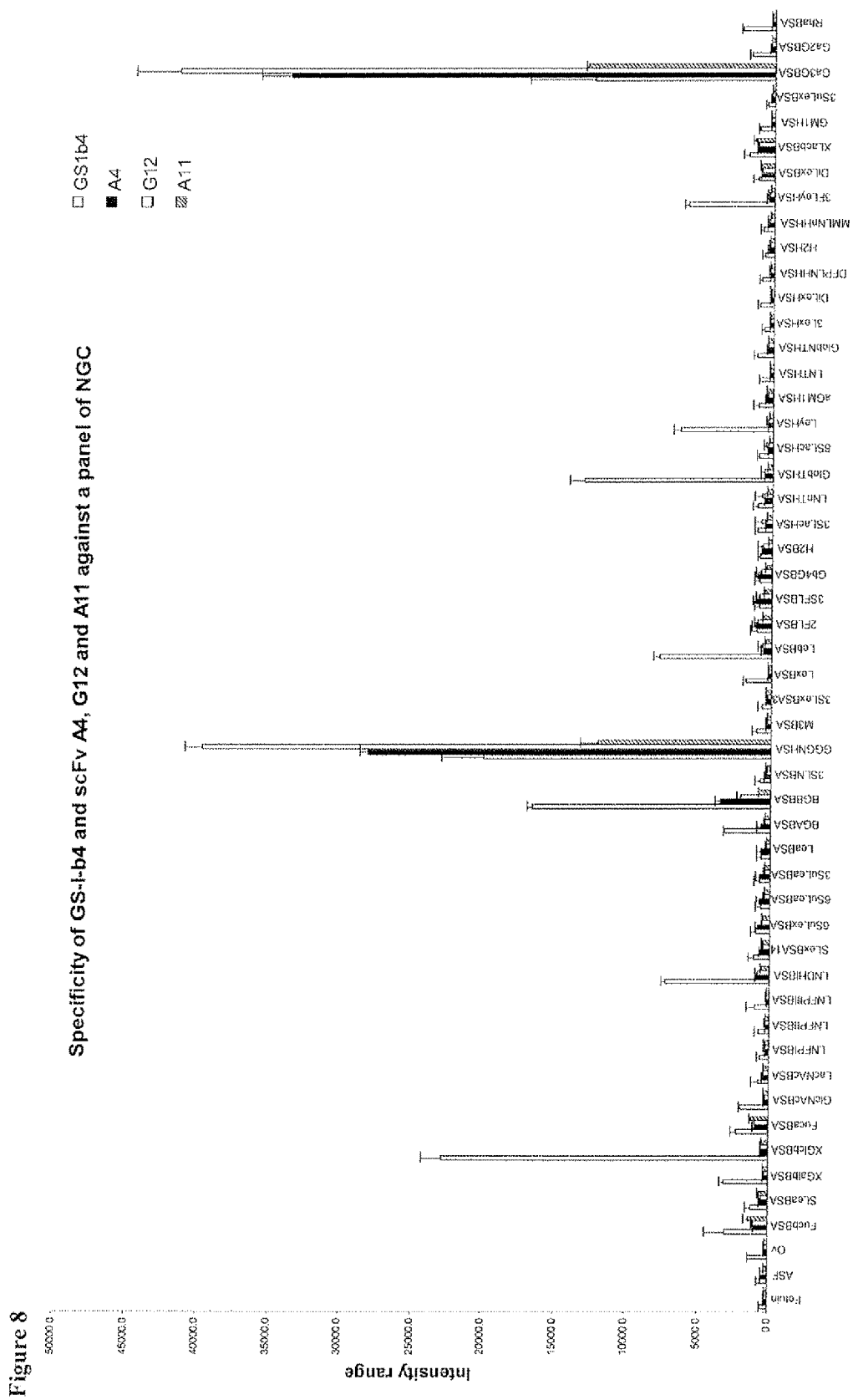
FIG. 8: Comparison of the specificity of selected scFv fragments A4, A11 and G12 against a panel of related NGCs compared directly to the specificity binding pattern of the lectin GS-1-B4, considered as highly specific for α-Gal residues.
Figure 12:
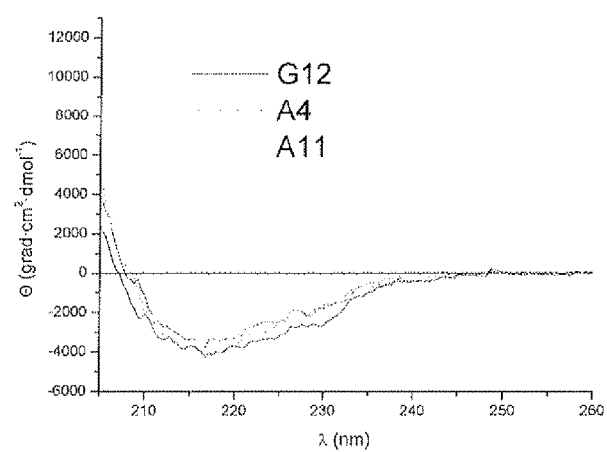
FIG. 12. Far UV CD spectra, expressed as molar ellipticity per residue, of scFvs in NaPi (10 mM)-NaCl (150 mM) pH 7.2 at 20° C.
Figure 15:
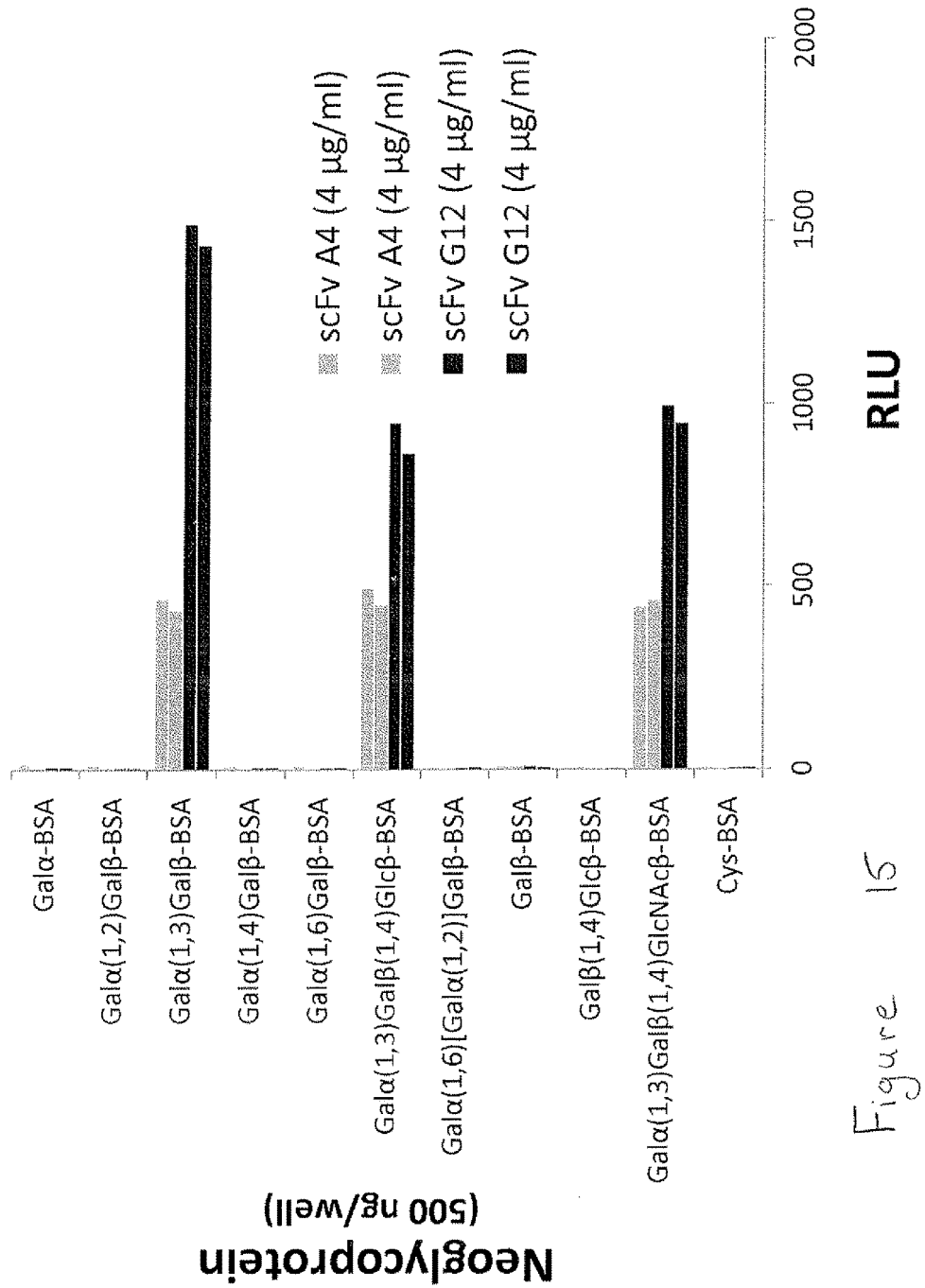
FIG. 15 CL-Elisa data for scFvs and neoglycoproteins showing relative luninescence.

The spectacular specificity of the scFvs has also been determined by analysis on an NGC microarray containing over 50 different structures. As shown in FIG. 8 the antibody fragments of the present invention, A4, G12 and A11, have a much higher specificity for the Gal-α-(1→3)-Gal epitope than does the prior art lectin, GS-1-B4. ScFv-based competitive ELISA. Competitive ELISAs were established with each of the three scFvs examined using as standard the free Gal-α-(1→3)-Gal disaccharide within the concentration range 0.001 to 10000 µg/ml (2.93 nM to 29.3 mM). The curves given by scFvs G12 and A4 were very similar with $ED_{50}$ values of 158 µg/ml and 311 µg/ml (0.46 and 0.91 mM), respectively (FIG. 6). ScFv A11 gave a less sensitive standard curve ($ED_{50}$=1225 µg/ml, 3.58 mM; FIG. 6). No standard curve could be generated with either the lectin GS-1-B4 or monoclonal M86 within the same concentration (data not shown). A panel of 21 related sugars were tested in the scFv-based competitive assays (Table 1). Of the sugars tested, only those bearing the Gal-α-(1,3)-Gal epitope demonstrated inhibition at detectable levels. All three scFvs were more reactive to the disaccharide than Gal-α-(1,3)-Gal-containing trisaccharides, as shown by lower inhibitory activity of the trisaccharides and supporting the results obtained in the direct ELISA. Also, scFvs A4 and A11 showed slightly higher inhibition (3 to 10%) when presented with the free tetrasaccharide (Gal-α-(1,3)-Gal-β-(1,4)-Gal-α-(1,3)-Gal), compared to the trisaccharides (Gal-α-(1,3)-Gal-β-(1,4)-Gal or Gal-α-(1,3)-Gal-β-(1,4)-Glc). No inhibition was observed in the presence of any monosaccharide within the ranges indicated, supporting the conclusion from the direct assay that monosaccharide structures are not capable of inhibiting binding to any of the scFvs to the Gal-α-(1,3)-Gal structure (Table 1).

Figure 7:
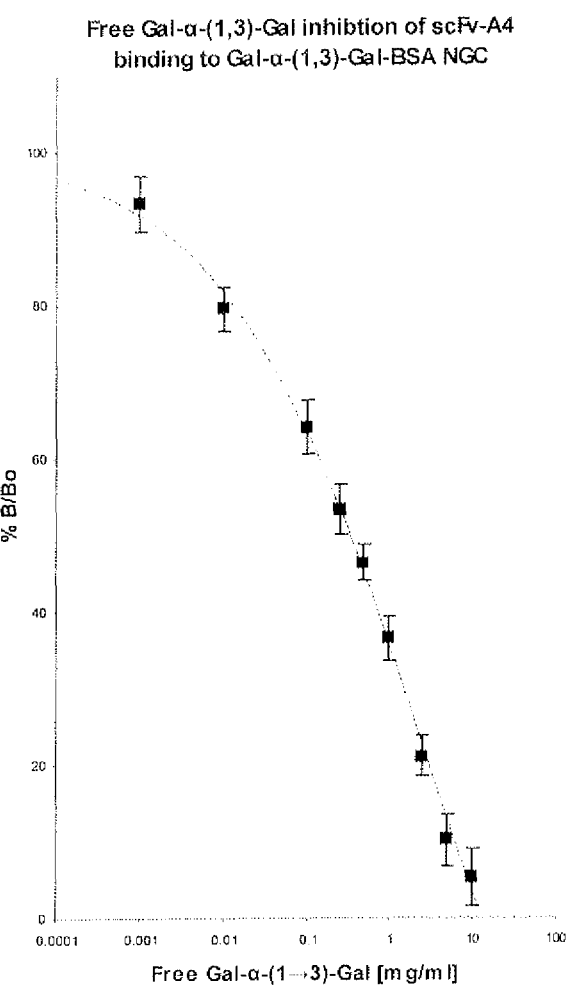
FIG. 7: Composite standard curve given by scFv-A4 from 9 independent runs.

ScFv A4 gave the most consistent readings and was selected for further in evaluation. FIG. 7 shows the A4 composite standard curve, giving an $ED_{50}$ of 327 µg/ml [0.95 mM] and detection limit of 3.9 ng/ml [~10 nM]. The assay was able to detect the Gal-α-(1→3)-Gal motif when protein bound in the form of NGCs and on the murine glycoprotein, laminin. The disaccharide NGC interacted with the scFvs in a similar manner to the free sugar, as indicated by the parallelism of the response obtained over the concentration range 0.25 to 1 mg/ml. Assay results indicated that 1 mg/ml of the Gal-α-(1→3)-Gal containing NGC contained 42 µg/ml of the disaccharide. This corresponded to a disaccharide:protein molar ratio of 9.4:1. The range as determined by MALDI trace is 10 to 25 residues, with an average of 16:1 per albumin. Similarly, the Gal-α-(1→3)-Gal-β-(1,4)-Gal containing NGC with glycan:protein molar ratio range of 15 to 31, with an average of 23:1 by MALDI was determined to have a molar incorporation ratio of 19.7:1 by competitive ELISA. Native laminin was too viscous to be analysed in the competitive ELISA. However, heat treatment reduced the viscosity and assay results indicated that there were 39 moles of the Gal-α-(1→3)-Gal residue per mole of murine laminin.

Affinity Values

Dissociation constants (Kd) for the scFvs were calculated from the measured association (kon) and dissociation (koff) rate constants by using surface plasmon resonance (SPR) BIAcore instrumentation and software (GE). Determined Kd's for the scFv are:

A4: $5.73 \times 10^{-8}$ M
G12: $1.80 \times 10^{-8}$ M
A11: $8.04 \times 10^{-9}$ M Under the same conditions, no binding was observed with the prior art lectin, GS-1-B4 or prior art monoclonal antibody, M86. In general, it is accepted that lectin-carbohydrate interactions are weaker than antigen-antibody interactions, with lectins having lower affinity constants in the range, $K_d=10^{-3}$ to $10^{-6}$ M for glycans. Thus the scFvs have greater affinity for their target glycan than existing binders.

With reported anti carbohydrate antibodies against a number of glycan epitopes having affinity constants in the range of $K_d=10^{-5}$ to $10^{-8}$ M (determined at steady state equilibrium in SPR) indicating that those scFv identified here in are amongst the highest affinity antibody fragments reported against glycan epitopes as defined by SPR.

Sequence Information

Seq Id No. 1 : Generic sequence of the fragments of the invention:

(SEQ ID NO: 1)
QAALTQPSSVS[T/A]NPGGTVKITCSGG[N/G/-][S/-][Y/-][G/-]

[G/-][S/-][G/Y][N/H/Y]YGWYQQKSPGSAPVTVIYSN[N/D][K/

Q/N]RPS[D/G]IPSRFSGS[T/K]S[G/D]ST[A/G/S]TLTITGVQ[V/

A]DDEAVY[F/Y]CG[A/S/T]YD[N/S][S/-][N/-][T/S]Y[V/A]G

[V/I]FGAGT[T/A]LTVLGQSSRSS[S/-]GGGSSGGGGSAVTLDESGGG

LQTPGG[G/A]LSLVCKASGFTFSSYSMQWVRQ[T/A]PGKGLEFVAGIG

[Y/N]SD[S/R]YTYFGPAVKGRATISRDNGQ[N/S]T[V/L]RLQLNNLR

AEDTATY[Y/F]CARS[A/G]D[T/S][I/G][Y/N]GCTHPWCSADNI

[D/N]AWGHGTEVIVSSTSGQAGQ

Unique individual sequences for each clone
Seq Id No. 2: scFv-A4
QAALTQPSSVSTNPGGTVKITCSGGNGNYGWYQQKSPGSAPVTVIYSNN

KRPSDIPSRFSGSKSGSTATLTITGVQVDDEAVYFCGAYDNTYVGVFGA

GTTLTVLGQSSRSSSGGGSSGGGGSAVTLDESGGGLQTPGGGLSLVCKA

SGFTFSSYSMQWVRQTPGKGLEFVAGIGYSDSYTYFGPAVKGRATISRD

NGQNTVRLQLNNLRAEDTATYYCARSADTIYGCTHPWCSADNIDAWGHG

TEVIVSSTSGQAGQ

Seq Id No. 3: scFv-G12
QAALTQPSSVSANPGETVKITCSGGSYHYGWYQQKSPGSAPVTVIYSNN

QRPSGIPSRFSGSTSDSTGTLTITGVQADDEAVYFCGSYDSSNTYAGIF

GAGTTLTVLGQSSRSSSGGGSSGGGGSAVTLDESGGGFQTPGGALSLVC

KASGFTFSSYSMQWVRQAPGKGLEFVAGIGNSDRYTYFGPAVKGRATIS

RDNGQSTLRLQLNNLRAEDTATYFCARSGDSGNGCTHPWCSADNINAWG

-continued

Sequence Information

HGTEVIVSSTSGQAGQ

Seq Id No. 4: scFv-A11
QAALTQPSSVSANPGETVKITCSGGGSYGGSYYYGWYQQKSPGSAPVTV

IYSNDNRPSDIPSRFSGSTSGSTSTLTITGVQVDDEAVYYCGTYDSSYV

GIFGAGTALTVLGQSSRSSGGGSSGGGGSAVTLDESGGGLQTPGGGLSL

VCKASGFTFSSYSMQWVRQTPGKGLEFVAGIGYSDSYTYFGPAVKGRAT

ISRDNGQNTVRLQLNNLRAEDTATYYCARSADTIYGCTHPWCSADNIDA

WGHGTEVIVSSTSGQAGQ

[ ] indicating a transition;
- indicating deletion scFvs: Interaction Studies by Circular Dichroism The scFvs A4, A11 and G12 were used to check their interaction with Galα(1,3)Galβ1-OMe (Carbosynth) and with melibiose, the latter as negative control.

Two types of experiments were performed: firstly, the near UV circular dichroism (CD) spectra of the scFvs in the absence and presence of 4 mM of both disaccharides have been compared. Secondly, the effect of the disaccharides on the thermal stability of the scFvs has been studied.

Experimental Procedure:

Samples were diluted in NaPi (10 mM)-NaCl (150 mM) pH 7.2 and either concentrated by ultrafiltration twice (for small amounts) or exhaustively dialyzed. CD spectra were acquired at 20° C. in a J-810 spectropolarimeter, equipped with a Peltier temperature control system, using a bandwidth of 1 nm, a scan rate of 20 nm/min and a response time of 4 s, collecting data every 0.2 nm and 3 accumulations for each spectrum. Near-UV spectra were registered at around 1.0 mg ml$^{-1}$ protein concentration in 1-cm path-length cells while far-UV spectra were recorded in 0.1 cm path-length quartz cells at a protein concentration of around 0.2 mg ml$^{-1}$. For all CD spectra, the corresponding buffer baseline was subtracted. Thermal stability was evaluated by measuring ellipticity changes at 208 nm while increasing temperature from 20 to 90° C., with a constant rate of 40° C./h. Ellipticity changes were collected every 0.2° C. and spectra were collected every 10° C. The thermal denaturation profiles were fitted to a sigmoidal function using the equation:—

$$\Theta(T) = \Theta_N + \sum_{i=1}^{n} \Delta\Theta_i \{\exp[-HD_i(T_{mi} - T)/R \cdot T_{mi} \cdot T]\}/\{1 + \exp[-HD_i(T_{mi} - T)/R \cdot T_{mi} \cdot T]\}$$

where $\Theta(T)$ represents the ellipticity at temperature T (Kelvin), $\Theta_N$ the ellipticity of the native protein, n the number of transitions, $\Delta\Theta_i$ the ellipticity increment of transition i, R the gas constant and $T_{mi}$ and $HD_i$ the temperature at the transition midpoint (melting temperature) and the parameter which describes the cooperativity (slope) of the corresponding transition, respectively.

Results:

In general, molar ellipticity values per residue in the near CD were between −80 and 40 grad·cm$^2$·dmol$^{-1}$ for the three scFvs, which tend to be low in terms of usual values in proteins. Starting with G12, the spectrum (in black, FIG. 1A) showed negative ellipticity between 250-280 nm (region dominated by Phe and Tyr electronic transitions) and a small positive band at 292 nm (region dominated by Trp electronic transitions). While melibiose did not cause any significant changes in the shape/intensity of the spectrum (spectrum in red, FIG. 1A), a clear change was detected in the presence of Galα(1,3)Galβ1-OMe: the band at 292 nm tended to disappear while higher negative values were observed in the 250-290 nm region (spectrum in green, FIG. 1A). Thus, the spectrum in the presence of Galα(1,3)Galβ1-OMe seems to indicate a change in the environment of aromatic residues contributing to the spectrum.

In the case of A4, the CD spectrum (in black, FIG. 1B) is also negative between 250 and 290 nm and there is a band (less intense than for G12) at 291 nm too. In addition, there is a clear negative band at 300 nm (assigned to Trp). As for G12, the effect of melibiose remained unchanged (spectrum in red, FIG. 1B). However, the molar ellipticity per residue in general decreased in the presence of Galα(1,3)Galβ1-OMe, especially between 260-280 nm, giving rise to lower negative values (spectrum in green, FIG. 1B). The band at 300 nm also showed a decrease in intensity, while the band at 291 nm hardly changed.

Regarding A11, the CD spectrum (in black, FIG. 1C) was similar to those of scFvs G12 and A4, with negative values of the molar ellipticity per residue between 250-290 nm and two bands, one positive at 292 nm and the second one negative at 302 nm. No significant changes were observed in the presence of either melibiose (spectrum in red, FIG. 1C) or Galα(1,3)Galβ1-OMe (spectrum in green, FIG. 1C). This indicates that, if there is any interaction with the sugar, the environment of the aromatic groups of the protein is not significantly affected.

In the second set of experiments, the thermal stability of the scFvs in the absence and presence of the disaccharides was investigated. With this type of experiment, we were able to get: 1) the far UV CD spectra at increasing temperatures, which gave information on changes in the secondary structure of the proteins upon heating and 2) the profile of the change in ellipticity at a certain wavelength, also with increasing temperatures, that allowed the calculation of the temperature of transition (Tm). Direct comparison of the Tm in the absence and presence of sugar provided information about the effect of the sugar on the scFvs, a thermal stabilisation (i.e. an increase in the Tm in the presence of the sugar) being indicative of interaction.

The far UV CD spectra of all scFvs at 20° C. showed positive values of molar ellipticity at short wavelengths (below 208 nm) and a negative band between 208-240 nm, features that are typical of β secondary structure (FIG. 2 and spectra in black in FIG. 3). FIG. 2 shows the good superimposition of the spectra for the three scFvs, which indicates a similar secondary structure for the three of them. No changes were observed in the spectra in the presence of either Galα(1,3)Galβ1-OMe (FIG. 3, spectra in green) or melibiose (not shown). After heating at 90° C., the positive band disappeared and the spectrum tended to higher negative values of ellipticity in almost the whole range of wavelengths (FIG. 3, spectra in red), indicating a loss of their native β secondary structure. The global change in the spectrum from 20° C. to 90° C. for G12 (FIG. 3A) and A4 (FIG. 3B) was similar in the absence or presence of the sugars; however, the final species after heating A11 are different in the absence and presence of Galα(1,3)Galβ1-OMe (FIG. 3, spectra in blue). This difference was not observed in the presence of melibiose.

Comparison of the profiles of the change in ellipticity at a given wavelength with increasing temperature (FIG. 4)

clearly showed that Galα(1,3)Galβ1-OMe induced an important stabilisation (between 7.7 and 10.2° C.) of the three scFvs (Table 1). On the contrary, the presence of melibiose did not result in a significant stabilisation (~0.2° C.) of either G12 or A11 (not checked for A4).

Denaturation was monitored at two different wavelengths for scFv G12 (Table 1). Comparative analysis of the effect of sugars on thermal stability of G12, by measuring changes in ellipticity at 218 nm in their absence and presence, shows that the addition of 4 mM melibiose does not alter either the $T_m$ or the HD (describing cooperativity) of the unfolding process, whereas the presence of 4 mM Galα(1,3)Galβ1-OMe increased both parameters. Data obtained at 208 nm also revealed an increment of 8.8° C. in the $T_m$ and a slightly more cooperative unfolding (+6.8 Kcal/mol) in the presence of Galα(1,3)Galβ1-OMe. For clarity, only denaturation profiles collected at 208 nm, in the absence and presence of Galα(1,3)Galβ1-OMe, are shown in FIG. 4A.

Furthermore, thermal denaturation experiments unequivocally demonstrated a stabilizing effect of Galα(1,3)Galβ1-OMe on the three scFvs, with a stabilisation of 10.2° C. for A4, 8.8° C. for G12 and 7.7° C. for A11.

DISCUSSION

Although known for over 30 years, there is still considerable interest in the Gal-α-(1,3)-Gal motif, commonly found as a terminal motif on glycoproteins and glycolipids in a range of species, with the exception of humans and chickens which lack the enzyme involved in the synthesis of the disaccharide. This glycan structure still remains relevant to xenotransplantation efforts and the potential to exploit the relatively large quantities of natural anti-Gal-α-(1,3)-Gal antibodies present in human serum to increase immunogenicity in cancer immunotherapy has been widely explored. Modification of cancer cells or cancer-associated molecules,

TABLE 1

Transition temperature ($T_m$) and cooperativity parameter (HD) of the thermal denaturation of scFvs in the absence and presence of 4 mM melibiose or Galα(1,3)Galβ1-OMe.

|  |  | scFv G12 | | scFv A4 | | scFv A11 | |
| --- | --- | --- | --- | --- | --- | --- | --- |
|  | λ | $T_m$ (° C.) | HD (Kcal/mol) | $T_m$ (° C.) | HD (Kcal/mol) | $T_m$ (° C.) | HD (Kcal/mol) |
| Pure | 218 | 66.4 ± 0.4* | 116 ± 21 | n.d. | n.d. | n.d. | n.d. |
|  | 208 | 64.7 ± 0.2** | 64 ± 4 | 64.6 ± 0.2** | 57 ± 3 | 61.3 ± 0.1* | 134 ± 7 |
| +melibiose | 218 | 66.5 ± 0.3* | 116 ± 16 | n.d. | n.d. | n.d. | n.d. |
|  | 208 | n.d. | n.d. | n.d. | n.d. | 61.1 ± 0.1* | 141 ± 7 |
| +Galα(1,3)Gal β1-OMe | 218 | 74.3 ± 0.4* | 137 ± 24 | n.d. | n.d. | n.d. | n.d. |
|  | 208 | 73.5 ± 0.3** | 71 ± 5 | 74.8 ± 0.3** | 52 ± 3 | 69.0 ± 0.2* | 95 ± 6 |

N.d.: not determined.
*Samples prepared by ultrafiltration.
**Samples prepared by dialysis.

As the change of molar ellipticity at 208 nm was significantly bigger than at 218 nm for G12 (see FIG. 3), monitoring at 208 nm was chosen for the rest of scFvs. In the case of A4, while the cooperativity of the process (shown in Table 1 and evidenced by the slope of the denaturation curve in FIG. 4B) did not change significantly (~4.7 Kcal/mol), the $T_m$ increased around 10° C. in the presence of 4 mM Galα(1,3)Galβ1-OMe. Finally, for A11, we observed a difference not only in the value of the $T_m$, but also in the cooperativity of the process, which is clearly higher than for G12 and A4 (Table 1), and in the molar ellipticity value at the end of the denaturation (Table 1 and FIG. 4C). While there is no significant difference between the curves obtained with or without melibiose, there is an increase of 7.7° C. in the $T_m$ of the antibody when Galα(1,3)Galβ1-OMe is present and interestingly, a large decrease in the cooperativity when comparing to the same scFv in the absence of this disaccharide (~38.5 Kcal/mol). When comparing to the cooperativity of the process for G12 and A4 in the presence of Galα(1,3)Galβ1-OMe, the value for the three proteins gets closer than in the absence of this disaccharide.

In summary, the results obtained clearly prove the existence of interaction between the three scFvs, A4, A11 and G12 and Galα(1,3)Galβ1-OMe. Moreover, the lack of interaction with melibiose evidences the specificity in the recognition. G12 showed a significant change in the near UV CD spectra, indicating that the binding of the disaccharide significantly affects the environment of aromatic residues.

such as mucins, with the Gal-α-(1,3)-Gal epitope has been shown to increase uptake by antigen-presenting cells and enhance the immune response. The ability to measure the loading of the motif on cells is important for this work, but the recently reported occurrence of this immunogenic motif on glycoprotein biopharmaceuticals, with resulting adverse reactions in patients, has particularly highlighted the need for specific binding agents and a convenient analytical method for Gal-α-(1,3)-Gal.

The most commonly utilised biomolecule for the detection and profiling of the Gal-α-(1→3)-Gal epitope is the lectin GS-1-B4, being highly specific for α-Gal residues. The affinity of GS-1-B4 to different α-Gal carbohydrates is a drawback in using this lectin as a reliable marker for Gal-α-(1→3)-Gal. The lectin from mushroom *Marasmius oreades* (MOA) has been reported to be more specific for Gal-α-(1,3)-Gal and Gal-α-(1,3)-Gal-β-(1,4)-GlcNAc epitopes, but yet binds strongly to the B blood group antigen, which contains an L-Fuc α-(1,2) linked to the Gal at the reducing end. Naturally occurring serum human antibodies against this and other non-human glycan epitopes have not been reliably used as an analytical tools. Traditional immunisation approaches are not very reliable for generation of high affinity antibodies against specific carbohydrate moieties and do not often yield antibodies with characteristics suitable for assay development. The use of phage display technology with recombinant antibody fragment libraries offers more promise, giving access to a larger repertoire of antibodies including anti-self antibodies that would not normally be available due to tolerisation. However, only a few successful examples have been published to date. The generation of antibodies toward carbohydrate moieties has to date been difficult due to their low affinity with only few successful examples published. The selection of initial library source and potential immunization regimes need careful thought and design, permitting for glycan presentation to mimic that was encountered under natural conditions. The selection here to utilize immunized chicken libraries allowed for single primers targeting the conserved regions flanking the unique functional $V_H$ and $V_L$ genes in to be amplified and fused as scFv. This enables the complete spectrum of rearranged variable fragments with subsequent cloning of highly diverse chicken immunoglobulin repertoires, as opposed to more complicated systems.

Chicken recombinant antibodies, like mouse or human derived antibodies, can be expressed in various forms (Fab or scFv), with a number of groups reporting the construction of chicken recombinant antibodies against a variety of protein targets. The optimization of panning conditions is keys to successful phage display against carbohydrate targets, taking into account the lower affinity of carbohydrate-protein interactions in comparison with protein-protein interactions.

Competitive binding assays are widely used for determination of low molecular weight compounds in complex samples, with often no viable alternative. They represent a versatile, robust assay configuration, being adaptable for high throughput or single-use, point-of-care formats. Competitive assays are, however, demanding in terms of the binding agent, with assay sensitivity being directly dependent on affinity of the binder for the analyte. We have demonstrated that all three scFvs that were purified could be used in competitive assays for Gal-α-(1,3)-Gal, allowing detection of the disaccharide at low ng/ml levels (detection limit estimated at 3.9 ng/ml [~10 nM]), which exceeds reported detection limits of most lectins, typically at the μg/ml level, when tested in similar plate assays. The exceptional specificity of the scFvs was also retained in this format. We have shown that the assay can detect the motif in the context of a glycoprotein and can be used to determine the level of incorporation of the motif on the protein. Thus, the assay provides the option of either direct analysis of the motif on a glycoprotein of interest or measurement of the disaccharide following release by, for example, the enzyme endo-beta-galactosidase C from *Clostridium perfringens*.

The observed differences in the CDR sequences between the three scFvs best characterised (scFv-G12, scFv-A4 and scFv-A11) may have resulted from a diverse in vivo population of Gal-α-(1→3)-Gal specific B cells in each individual animal or possibly from the pooled cDNA of the two animals used to produce the library. Several amino acid changes (S→Q; G→S) and deletions, typically serine, occurred in the linker sequences of each of the sequenced fragments. The modifications within the linker region did not appear to affect the stability or function of the linker significantly. Single scFv clones, induced in bacterial culture, produced soluble scFv that was readily purified by Ni-NTA chromatography. Without any optimization, the soluble yield was satisfactory and reproducible. scFv stability and presentation can be influenced by concentration, pH and temperature along with other factors. It is possible that individual preparation of scFvs may contain an unknown proportion of dimeric antibody, which is functionally bivalent and can lead to changes in observed kinetics.

The purified and tested scFv antibodies (A4, A11 and G12) demonstrated high specificity to the Gal-α-(1→3)-Gal epitope, which may indicate that they have future use as fine specificity reagents against this epitope.

TABLE 1

Specificity study of competitive ELISAs based on the three anti-gal-alpha1-3 gal scFvs

| Free Sugars | Highest concentration (mg/mL) | Inhibition observed (Y/N) | % Maximum inhibition at Max Conc | | |
|---|---|---|---|---|---|
| | | | A11 | A4 | G12 |
| gal-α(1,3)-gal-BSA (NGC) | at 1 mg/ml | Y | 51.06 | 36.4 | 33.93 |
| gal-α-(1,3)-gal-β-(1,4)-gal | 1 | Y | 76.83 | 68.18 | 64.43 |
| gal-α(1,3)-gal-β-(1,4)-glc | 1 | Y | 73.88 | 66.20 | 83.03 |
| gal-α(1,3)-gal-β-(1,4)-gal-α-(1,3)-gal | 1 | Y | 78.41 | 73.48 | 73.54 |
| Galcato-N-biose | 1 | N | / | / | / |
| 4β galactobiose | 1 | N | / | / | / |
| Laminarbiose | 1 | N | / | / | / |
| β1-4-D-Xylobiose | 1 | N | / | / | / |
| N-Acetyl-D-lactosamine . . . (LacNAc) | 1 | N | / | / | / |
| D-cellibiose | 10 | N | / | / | / |
| Melibiose | 10 | N | / | / | / |
| D-Raffinose | 10 | N | / | / | / |
| Lactulose | 10 | N | / | / | / |
| Palatinose | 10 | N | / | / | / |
| β-Gentibiose | 10 | N | / | / | / |
| D+ Trehalose | 10 | N | / | / | / |
| D+ Turanose | 10 | N | / | / | / |
| L- Frucose | 10 | N | / | / | / |
| D+ Glucose | 10 | N | / | / | / |
| Sucrose | 10 | N | / | / | / |
| N-Acetyl-D-glucoseamine . . . (GlcNAc) | 10 | N | / | / | / |
| Galactose | 10 | N | / | / | / |

The words "comprises/comprising" and the words "having/including" when used herein with reference to the present invention are used to specify the presence of stated features, integers, steps or components but does not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

REFERENCES

Andris-Widhopf J, Rader C, Steinberger P, Fuller R, Barbas C F (2000) Methods for the generation of chicken monoclonal antibody fragments by phage display. J. Immunological Methods 242:159-81 Available at: http://www.ncbi.nlm.nih.gov/pubmed/10986398.

Bosques C J, Collins B E, Meador J W, Sarvaiya H, Murphy J L, Dellorusso G, Bulik D a, Hsu I-H, Washburn N, Sipsey S F, Myette J R, Raman R, Shriver Z, Sasisekharan R, Venkataraman G (2010) Chinese hamster ovary cells can produce galactose-α-1,3-galactose antigens on proteins. Nature biotechnology 28:1153-6 Available at: http://www.ncbi.nlm.nih.gov/pubmed/21057479 [Accessed Aug. 12, 2011].

The invention claimed is:

1. An antibody capable of binding selectively to Gal-α-(1→3)-Gal epitope, the antibody comprising SEQ ID NOs 2, 3 or 4.

2. The antibody of claim 1 wherein the antibody is a monoclonal antibody.

3. The antibody of claim 2, wherein the antibody comprises SEQ ID No. 2.

4. An assay kit for the determination of the presence or the quantification of a Gal-α-(1→3)-Gal motif in tissues or cells or on proteins, comprising the antibody of claim 1.

5. The assay kit of claim 4 further comprising reagents and/or instructions for an ELISA assay, a competition/inhibition ELISA assay, a sandwich ELISA assay, a microarray based assay, a rapid assay platform which comprises quantum dots or fluorescent tags, an immunohistochemistry assay, or a flow cytometry assay.

6. A method of detecting the presence of, or quantifying the amount of a Gal-α-(1→3)-Gal motif in tissues or cells or on proteins, comprising detecting and determining the degree of binding of the antibody of claim 1 to the tissue, cell or protein.

7. A composition comprising the antibody of claim 1 together with a pharmaceutically acceptable carrier or excipient.

8. A method for the detection of a Gal-α-(1→3)-Gal epitope in a sample comprising contacting a sample comprising the epitope with the antibody of claim 1 and detecting the antibody bound to the sample.

* * * * *

SEQUENCE LISTING

<160> NUMBER OF SEQ ID NOS: 11

<210> SEQ ID NO 1
<211> LENGTH: 266
<212> TYPE: PRT
<213> ORGANISM: Artificial Sequence
<220> FEATURE:
<223> OTHER INFORMATION: Synthetic generic sequence for engineered
      single chain antibody fragment for detecting non-human Gal-alpha-
      (1-3)-Gal carbohydrate epitope
<220> FEATURE:
<221> NAME/KEY: VARIANT
<222> LOCATION: 12
<223> OTHER INFORMATION: X is T or A
<220> FEATURE:
<221> NAME/KEY: VARIANT
<222> LOCATION: 16
<223> OTHER INFORMATION: X is G or E
<220> FEATURE:
<221> NAME/KEY: VARIANT
<222> LOCATION: (26)..(33)
<223> OTHER INFORMATION: X is a multi aa sequence comprising [N or G or
      absent],[S or absent], [Y or absent], [G or absent], [G or
      absent], [S or absent], [G or Y] and [N or H or Y]
<220> FEATURE:
<221> NAME/KEY: VARIANT
<222> LOCATION: (54)..(55)
<223> OTHER INFORMATION: X is a multi aa seqence comprising [N or D] and
      [K or Q or N]
<220> FEATURE:
<221> NAME/KEY: VARIANT
<222> LOCATION: 59
<223> OTHER INFORMATION: X is D or G
<220> FEATURE:
<221> NAME/KEY: VARIANT
<222> LOCATION: 68
<223> OTHER INFORMATION: X is T or K
<220> FEATURE:
<221> NAME/KEY: VARIANT
<222> LOCATION: 70
<223> OTHER INFORMATION: X is G or D
<220> FEATURE:
<221> NAME/KEY: VARIANT
<222> LOCATION: 73
<223> OTHER INFORMATION: X is A or G or S
<220> FEATURE:
<221> NAME/KEY: VARIANT
<222> LOCATION: 82
<223> OTHER INFORMATION: X is A or V
<220> FEATURE:
<221> NAME/KEY: VARIANT
<222> LOCATION: 89
<223> OTHER INFORMATION: X is F or Y
<220> FEATURE:
<221> NAME/KEY: VARIANT
<222> LOCATION: 92
<223> OTHER INFORMATION: X is A or S or T
<220> FEATURE:
<221> NAME/KEY: VARIANT
<222> LOCATION: (95)..(98)
<223> OTHER INFORMATION: X is a multi aa sequence comprising [N or S],
      [S or absent], [N or absent] and [T or S]
<220> FEATURE:
<221> NAME/KEY: VARIANT
<222> LOCATION: 100
<223> OTHER INFORMATION: X is V or A
<220> FEATURE:
<221> NAME/KEY: VARIANT
<222> LOCATION: 102
<223> OTHER INFORMATION: X is V or I
<220> FEATURE:
<221> NAME/KEY: VARIANT
<222> LOCATION: 108
<223> OTHER INFORMATION: X is T or A
<220> FEATURE:
<221> NAME/KEY: VARIANT
<222> LOCATION: 120
<223> OTHER INFORMATION: X is S or absent

```
<220> FEATURE:
<221> NAME/KEY: VARIANT
<222> LOCATION: 141
<223> OTHER INFORMATION: X is L or F
<220> FEATURE:
<221> NAME/KEY: VARIANT
<222> LOCATION: 147
<223> OTHER INFORMATION: X is G or A
<220> FEATURE:
<221> NAME/KEY: VARIANT
<222> LOCATION: 170
<223> OTHER INFORMATION: X is T or A
<220> FEATURE:
<221> NAME/KEY: VARIANT
<222> LOCATION: 183
<223> OTHER INFORMATION: X is Y or N
<220> FEATURE:
<221> NAME/KEY: VARIANT
<222> LOCATION: 186
<223> OTHER INFORMATION: X is S or R
<220> FEATURE:
<221> NAME/KEY: VARIANT
<222> LOCATION: 207
<223> OTHER INFORMATION: X is N or S
<220> FEATURE:
<221> NAME/KEY: VARIANT
<222> LOCATION: 209
<223> OTHER INFORMATION: X is V or L
<220> FEATURE:
<221> NAME/KEY: VARIANT
<222> LOCATION: 225
<223> OTHER INFORMATION: X is Y or F
<220> FEATURE:
<221> NAME/KEY: VARIANT
<222> LOCATION: 230
<223> OTHER INFORMATION: X is A or G
<220> FEATURE:
<221> NAME/KEY: VARIANT
<222> LOCATION: (232)..(234)
<223> OTHER INFORMATION: X is a multi aa sequence comprising [T or S],
     [I or G] and [Y or N]
<220> FEATURE:
<221> NAME/KEY: VARIANT
<222> LOCATION: 247
<223> OTHER INFORMATION: X is D or N

<400> SEQUENCE: 1

Gln Ala Ala Leu Thr Gln Pro Ser Ser Val Ser Xaa Asn Pro Gly Xaa
1               5                   10                  15

Thr Val Lys Ile Thr Cys Ser Gly Gly Xaa Xaa Xaa Xaa Xaa Xaa Xaa
            20                  25                  30

Xaa Tyr Gly Trp Tyr Gln Gln Lys Ser Pro Gly Ser Ala Pro Val Thr
                35                  40                  45

Val Ile Tyr Ser Asn Xaa Xaa Arg Pro Ser Xaa Ile Pro Ser Arg Phe
        50                  55                  60

Ser Gly Ser Xaa Ser Xaa Ser Thr Xaa Thr Leu Thr Ile Thr Gly Val
65                  70                  75                  80

Gln Xaa Asp Asp Glu Ala Val Tyr Xaa Cys Gly Xaa Tyr Asp Xaa Xaa
                85                  90                  95

Xaa Xaa Tyr Xaa Gly Xaa Phe Gly Ala Gly Thr Xaa Leu Thr Val Leu
            100                 105                 110

Gly Gln Ser Ser Arg Ser Ser Xaa Gly Gly Gly Ser Ser Gly Gly Gly
            115                 120                 125

Gly Ser Ala Val Thr Leu Asp Glu Ser Gly Gly Xaa Gln Thr Pro
        130                 135                 140

Gly Gly Xaa Leu Ser Leu Val Cys Lys Ala Ser Gly Phe Thr Phe Ser
145                 150                 155                 160

Ser Tyr Ser Met Gln Trp Val Arg Gln Xaa Pro Gly Lys Gly Leu Glu
```

```
                    165                 170                 175
Phe Val Ala Gly Ile Gly Xaa Ser Asp Xaa Tyr Thr Tyr Phe Gly Pro
                180                 185                 190

Ala Val Lys Gly Arg Ala Thr Ile Ser Arg Asp Asn Gly Gln Xaa Thr
            195                 200                 205

Xaa Arg Leu Gln Leu Asn Asn Leu Arg Ala Glu Asp Thr Ala Thr Tyr
        210                 215                 220

Xaa Cys Ala Arg Ser Xaa Asp Xaa Xaa Xaa Gly Cys Thr His Pro Trp
225                 230                 235                 240

Cys Ser Ala Asp Asn Ile Xaa Ala Trp Gly His Gly Thr Glu Val Ile
                245                 250                 255

Val Ser Ser Thr Ser Gly Gln Ala Gly Gln
                260                 265

<210> SEQ ID NO 2
<211> LENGTH: 259
<212> TYPE: PRT
<213> ORGANISM: Artificial Sequence
<220> FEATURE:
<223> OTHER INFORMATION: Synthetic protein sequence for scFv-A4
      antibody fragment for detecting non-human Gal-alpha(1-3)-Gal

<400> SEQUENCE: 2

Gln Ala Ala Leu Thr Gln Pro Ser Ser Val Ser Thr Asn Pro Gly Gly
1               5                   10                  15

Thr Val Lys Ile Thr Cys Ser Gly Gly Asn Gly Asn Tyr Gly Trp Tyr
                20                  25                  30

Gln Gln Lys Ser Pro Gly Ser Ala Pro Val Thr Val Ile Tyr Ser Asn
            35                  40                  45

Asn Lys Arg Pro Ser Asp Ile Pro Ser Arg Phe Ser Gly Ser Lys Ser
        50                  55                  60

Gly Ser Thr Ala Thr Leu Thr Ile Thr Gly Val Gln Val Asp Asp Glu
65                  70                  75                  80

Ala Val Tyr Phe Cys Gly Ala Tyr Asp Asn Thr Tyr Val Gly Val Phe
                85                  90                  95

Gly Ala Gly Thr Thr Leu Thr Val Leu Gly Gln Ser Ser Arg Ser Ser
            100                 105                 110

Ser Gly Gly Gly Ser Ser Gly Gly Gly Ser Ala Val Thr Leu Asp
        115                 120                 125

Glu Ser Gly Gly Gly Leu Gln Thr Pro Gly Gly Gly Leu Ser Leu Val
130                 135                 140

Cys Lys Ala Ser Gly Phe Thr Phe Ser Ser Tyr Ser Met Gln Trp Val
145                 150                 155                 160

Arg Gln Thr Pro Gly Lys Gly Leu Glu Phe Val Ala Gly Ile Gly Tyr
                165                 170                 175

Ser Asp Ser Tyr Thr Tyr Phe Gly Pro Ala Val Lys Gly Arg Ala Thr
            180                 185                 190

Ile Ser Arg Asp Asn Gly Gln Asn Thr Val Arg Leu Gln Leu Asn Asn
        195                 200                 205

Leu Arg Ala Glu Asp Thr Ala Thr Tyr Tyr Cys Ala Arg Ser Ala Asp
    210                 215                 220

Thr Ile Tyr Gly Cys Thr His Pro Trp Cys Ser Ala Asp Asn Ile Asp
225                 230                 235                 240

Ala Trp Gly His Gly Thr Glu Val Ile Val Ser Ser Thr Ser Gly Gln
                245                 250                 255
```

Ala Gly Gln

<210> SEQ ID NO 3
<211> LENGTH: 261
<212> TYPE: PRT
<213> ORGANISM: Artificial Sequence
<220> FEATURE:
<223> OTHER INFORMATION: Synthetic protein sequence for scFv-G12
    antibody fragment for detecting non-human Gal-alpha(1-3)-Gal

<400> SEQUENCE: 3

Gln Ala Ala Leu Thr Gln Pro Ser Ser Val Ser Ala Asn Pro Gly Glu
1               5                   10                  15

Thr Val Lys Ile Thr Cys Ser Gly Gly Ser Tyr His Tyr Gly Trp Tyr
            20                  25                  30

Gln Gln Lys Ser Pro Gly Ser Ala Pro Val Thr Val Ile Tyr Ser Asn
        35                  40                  45

Asn Gln Arg Pro Ser Gly Ile Pro Ser Arg Phe Ser Gly Ser Thr Ser
    50                  55                  60

Asp Ser Thr Gly Thr Leu Thr Ile Thr Gly Val Gln Ala Asp Asp Glu
65                  70                  75                  80

Ala Val Tyr Phe Cys Gly Ser Tyr Asp Ser Ser Asn Thr Tyr Ala Gly
                85                  90                  95

Ile Phe Gly Ala Gly Thr Thr Leu Thr Val Leu Gly Gln Ser Ser Arg
            100                 105                 110

Ser Ser Ser Gly Gly Gly Ser Gly Gly Gly Gly Ser Ala Val Thr
        115                 120                 125

Leu Asp Glu Ser Gly Gly Phe Gln Thr Pro Gly Gly Ala Leu Ser
    130                 135                 140

Leu Val Cys Lys Ala Ser Gly Phe Thr Phe Ser Ser Tyr Ser Met Gln
145                 150                 155                 160

Trp Val Arg Gln Ala Pro Gly Lys Gly Leu Glu Phe Val Ala Gly Ile
                165                 170                 175

Gly Asn Ser Asp Arg Tyr Thr Tyr Phe Gly Pro Ala Val Lys Gly Arg
            180                 185                 190

Ala Thr Ile Ser Arg Asp Asn Gly Gln Ser Thr Leu Arg Leu Gln Leu
        195                 200                 205

Asn Asn Leu Arg Ala Glu Asp Thr Ala Thr Tyr Phe Cys Ala Arg Ser
    210                 215                 220

Gly Asp Ser Gly Asn Gly Cys Thr His Pro Trp Cys Ser Ala Asp Asn
225                 230                 235                 240

Ile Asn Ala Trp Gly His Gly Thr Glu Val Ile Val Ser Ser Thr Ser
                245                 250                 255

Gly Gln Ala Gly Gln
            260

<210> SEQ ID NO 4
<211> LENGTH: 263
<212> TYPE: PRT
<213> ORGANISM: Artificial Sequence
<220> FEATURE:
<223> OTHER INFORMATION: Synthetic protein sequence forscFv-A11
    antibody fragment for detecting non-human Gal-alpha(1-3)-Gal

<400> SEQUENCE: 4

Gln Ala Ala Leu Thr Gln Pro Ser Ser Val Ser Ala Asn Pro Gly Glu
1               5                   10                  15

Thr Val Lys Ile Thr Cys Ser Gly Gly Gly Ser Tyr Gly Gly Ser Tyr

```
                    20                  25                  30
Tyr Tyr Gly Trp Tyr Gln Gln Lys Ser Pro Gly Ser Ala Pro Val Thr
            35                  40                  45

Val Ile Tyr Ser Asn Asp Asn Arg Pro Ser Asp Ile Pro Ser Arg Phe
        50                  55                  60

Ser Gly Ser Thr Ser Gly Ser Thr Ser Thr Leu Thr Ile Thr Gly Val
65                  70                  75                  80

Gln Val Asp Asp Glu Ala Val Tyr Tyr Cys Gly Thr Tyr Asp Ser Ser
                85                  90                  95

Tyr Val Gly Ile Phe Gly Ala Gly Thr Ala Leu Thr Val Leu Gly Gln
            100                 105                 110

Ser Ser Arg Ser Ser Gly Gly Ser Ser Gly Gly Gly Ser Ala
        115                 120                 125

Val Thr Leu Asp Glu Ser Gly Gly Gly Leu Gln Thr Pro Gly Gly Gly
    130                 135                 140

Leu Ser Leu Val Cys Lys Ala Ser Gly Phe Thr Phe Ser Ser Tyr Ser
145                 150                 155                 160

Met Gln Trp Val Arg Gln Thr Pro Gly Lys Gly Leu Glu Phe Val Ala
                165                 170                 175

Gly Ile Gly Tyr Ser Asp Ser Tyr Thr Tyr Phe Gly Pro Ala Val Lys
            180                 185                 190

Gly Arg Ala Thr Ile Ser Arg Asp Asn Gly Gln Asn Thr Val Arg Leu
        195                 200                 205

Gln Leu Asn Asn Leu Arg Ala Glu Asp Thr Ala Thr Tyr Tyr Cys Ala
    210                 215                 220

Arg Ser Ala Asp Thr Ile Tyr Gly Cys Thr His Pro Trp Cys Ser Ala
225                 230                 235                 240

Asp Asn Ile Asp Ala Trp Gly His Gly Thr Glu Val Ile Val Ser Ser
                245                 250                 255

Thr Ser Gly Gln Ala Gly Gln
            260

<210> SEQ ID NO 5
<211> LENGTH: 11
<212> TYPE: PRT
<213> ORGANISM: Artificial Sequence
<220> FEATURE:
<223> OTHER INFORMATION: Synthetic Variable Light Chain Sequence 1 of an
      antibody for detecting non-human Gal-alpha(1-3)-Gal
<220> FEATURE:
<221> NAME/KEY: VARIANT
<222> LOCATION: 4
<223> OTHER INFORMATION: X is N or G or absent
<220> FEATURE:
<221> NAME/KEY: VARIANT
<222> LOCATION: 5
<223> OTHER INFORMATION: X is S or absent
<220> FEATURE:
<221> NAME/KEY: VARIANT
<222> LOCATION: 6
<223> OTHER INFORMATION: X is Y or absent
<220> FEATURE:
<221> NAME/KEY: VARIANT
<222> LOCATION: 7
<223> OTHER INFORMATION: X is GG or absent
<220> FEATURE:
<221> NAME/KEY: VARIANT
<222> LOCATION: 8
<223> OTHER INFORMATION: X is S or absent
<220> FEATURE:
<221> NAME/KEY: VARIANT
<222> LOCATION: 9
<223> OTHER INFORMATION: X is Y or G or absent
```

```
<220> FEATURE:
<221> NAME/KEY: VARIANT
<222> LOCATION: 10
<223> OTHER INFORMATION: X is N or H or Y

<400> SEQUENCE: 5

Ser Gly Gly Xaa Xaa Xaa Xaa Xaa Xaa Xaa Tyr
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Synthetic Variable Light Chain Sequence 2 of an
      antibody for detecting non-human Gal-alpha(1-3)-Gal
<220> FEATURE:
<221> NAME/KEY: VARIANT
<222> LOCATION: 3
<223> OTHER INFORMATION: X is N or D
<220> FEATURE:
<221> NAME/KEY: VARIANT
<222> LOCATION: 4
<223> OTHER INFORMATION: X is K or N or Q

<400> SEQUENCE: 6

Ser Asn Xaa Xaa Arg Pro Ser
1               5

<210> SEQ ID NO 7
<211> LENGTH: 12
<212> TYPE: PRT
<213> ORGANISM: Artificial Sequence
<220> FEATURE:
<223> OTHER INFORMATION: Synthetic Variable Light Chain Sequence 3 of an
      antibody for detecting non-human Gal-alpha(1-3)-Gal
<220> FEATURE:
<221> NAME/KEY: VARIANT
<222> LOCATION: 2
<223> OTHER INFORMATION: X is A, T or S
<220> FEATURE:
<221> NAME/KEY: VARIANT
<222> LOCATION: 5
<223> OTHER INFORMATION: X is S or N
<220> FEATURE:
<221> NAME/KEY: VARIANT
<222> LOCATION: 6
<223> OTHER INFORMATION: X is S or absent
<220> FEATURE:
<221> NAME/KEY: VARIANT
<222> LOCATION: 7
<223> OTHER INFORMATION: X is N or absent
<220> FEATURE:
<221> NAME/KEY: VARIANT
<222> LOCATION: 8
<223> OTHER INFORMATION: X is T or S
<220> FEATURE:
<221> NAME/KEY: VARIANT
<222> LOCATION: 10
<223> OTHER INFORMATION: X is V or A
<220> FEATURE:
<221> NAME/KEY: VARIANT
<222> LOCATION: 12
<223> OTHER INFORMATION: X is V or I

<400> SEQUENCE: 7

Gly Xaa Tyr Asp Xaa Xaa Xaa Xaa Tyr Xaa Gly Xaa
1               5                   10

<210> SEQ ID NO 8
<211> LENGTH: 10
<212> TYPE: PRT
<213> ORGANISM: Artificial Sequence
```

```
<220> FEATURE:
<223> OTHER INFORMATION: Synthetic Variable heavy chain sequence 5 of an
      antibody for detecting non-human Gal-alpha(1-3)-Gal

<400> SEQUENCE: 8

Gly Phe Thr Phe Ser Ser Tyr Ser Met Gln
1               5                   10

<210> SEQ ID NO 9
<211> LENGTH: 14
<212> TYPE: PRT
<213> ORGANISM: Artificial Sequence
<220> FEATURE:
<221> NAME/KEY: VARIANT
<222> LOCATION: 1
<223> OTHER INFORMATION: X is Y or N
<220> FEATURE:
<223> OTHER INFORMATION: Synthetic Variable heavy chain sequence 6 of an
      antibody for detecting non-human Gal-alpha(1-3)-Gal
<220> FEATURE:
<221> NAME/KEY: VARIANT
<222> LOCATION: 4
<223> OTHER INFORMATION: X is S or R

<400> SEQUENCE: 9

Xaa Ser Asp Xaa Tyr Thr Tyr Phe Gly Pro Ala Val Lys Gly
1               5                   10

<210> SEQ ID NO 10
<211> LENGTH: 18
<212> TYPE: PRT
<213> ORGANISM: Artificial Sequence
<220> FEATURE:
<223> OTHER INFORMATION: Synthetic Variable heavy chain sequence 7 of an
      antibody for detecting non-human Gal-alpha(1-3)-Gal
<220> FEATURE:
<221> NAME/KEY: VARIANT
<222> LOCATION: 2
<223> OTHER INFORMATION: X is A or G
<220> FEATURE:
<221> NAME/KEY: VARIANT
<222> LOCATION: 4
<223> OTHER INFORMATION: X is TIY or SGN
<220> FEATURE:
<221> NAME/KEY: VARIANT
<222> LOCATION: 17
<223> OTHER INFORMATION: X is D or N

<400> SEQUENCE: 10

Ser Xaa Asp Xaa Gly Cys Thr His Pro Trp Cys Ser Ala Asp Asn Ile
1               5                   10                  15

Xaa Ala

<210> SEQ ID NO 11
<211> LENGTH: 18
<212> TYPE: PRT
<213> ORGANISM: Artificial Sequence
<220> FEATURE:
<223> OTHER INFORMATION: Synthetic Linker Sequence 9 of an antibody for
      detecting non-human Gal-alpha(1-3)-Gal
<220> FEATURE:
<221> NAME/KEY: VARIANT
<222> LOCATION: 8
<223> OTHER INFORMATION: X is S or absent

<400> SEQUENCE: 11

Gly Gln Ser Ser Arg Ser Ser Xaa Gly Gly Gly Ser Ser Gly Gly Gly
1               5                   10                  15

Gly Ser
```